United States Patent
Koehler

(10) Patent No.: US 9,320,923 B2
(45) Date of Patent: Apr. 26, 2016

(54) SURGICAL FACE MASK, INCLUDING REUSABLE MASKS, WITH FILTERED INHALATION AND EXHALATION VALVES

(76) Inventor: Richard H. Koehler, Plymouth, MA (US)

( * ) Notice: Subject to any disclaimer, the term of this patent is extended or adjusted under 35 U.S.C. 154(b) by 1111 days.

(21) Appl. No.: 13/284,646

(22) Filed: Oct. 28, 2011

(65) Prior Publication Data

US 2012/0103339 A1    May 3, 2012

Related U.S. Application Data

(63) Continuation-in-part of application No. PCT/US2010/033037, filed on Apr. 29, 2010.

(60) Provisional application No. 61/173,927, filed on Apr. 29, 2009.

(51) Int. Cl.

| | | |
|---|---|---|
| *A61B 18/02* | (2006.01) | |
| *A41D 13/11* | (2006.01) | |
| *A62B 18/02* | (2006.01) | |
| *A61M 16/06* | (2006.01) | |

(52) U.S. Cl.
CPC .......... *A62B 18/025* (2013.01); *A41D 13/1146* (2013.01); *A62B 18/02* (2013.01); *A61M 2016/0661* (2013.01)

(58) Field of Classification Search
CPC ............ A61M 16/06; A61M 16/0605; A61M 16/0661; A61M 16/0683; A61M 16/0688; A62B 7/00; A62B 7/10; A62B 9/00; A62B 9/006; A62B 9/02; A62B 18/00; A62B 18/02; A62B 18/025; A62B 18/08; A62B 18/084; A62B 18/088; A62B 18/10; A62B 23/00; A62B 23/02; A62B 23/025; A41D 13/11–13/1146; A41D 13/1161–13/1176; A41D 13/1192
See application file for complete search history.

(56) References Cited

U.S. PATENT DOCUMENTS

| | | | | |
|---|---|---|---|---|
| 4,373,520 | A * | 2/1983 | Arbique ................... | 128/201.19 |
| 5,003,633 | A * | 4/1991 | Itoh ......................... | 2/9 |
| 5,090,407 | A * | 2/1992 | Lesage et al. ............ | 128/205.27 |
| 5,419,318 | A | 5/1995 | Tayebi | |
| 5,823,188 | A | 10/1998 | Harges, Jr. et al. | |
| 6,102,040 | A | 8/2000 | Tayebi et al. | |
| 6,182,660 | B1 * | 2/2001 | Hopper ................... | A61F 11/00 |
| | | | | 128/200.24 |

(Continued)

FOREIGN PATENT DOCUMENTS

EP    1285594    11/2009

OTHER PUBLICATIONS

Amazon, Oct. 28, 2014, 3M P100 Particulate Respirator Mask #8293, http://www.amazon.com/3M-P100-Particulate-Respirator, pp. 1.

(Continued)

*Primary Examiner* — Rachel Young
(74) *Attorney, Agent, or Firm* — Knobbe, Martens, Olson & Bear LLP

(57) ABSTRACT

Face masks that can be used, for example, in medical and surgical procedures, including both completely or partially disposable and reusable masks, that can be custom fitted to the wearer, and which can include one or more filtering inhalation and exhalation valves and/or compartments allowing for separated filtering of inhalation and exhalation gases. Some embodiments include systems, methods and kits for reducing contaminants in an inhalation and exhalation flow stream.

25 Claims, 14 Drawing Sheets

(56) References Cited

U.S. PATENT DOCUMENTS

| | | | |
|---|---|---|---|
| 6,196,223 B1* | 3/2001 | Belfer | A41D 13/1176 |
| | | | 128/205.25 |
| 6,214,094 B1* | 4/2001 | Rousseau et al. | 96/15 |
| 6,532,598 B1* | 3/2003 | Cardarelli | A41D 13/11 |
| | | | 128/206.19 |
| 6,805,124 B2 | 10/2004 | Japuntich et al. | |
| 6,978,782 B2 | 12/2005 | Tayebi | |
| 7,044,126 B2 | 5/2006 | Gavriely | |
| 2002/0185133 A1* | 12/2002 | Japuntich et al. | 128/206.12 |
| 2003/0136410 A1* | 7/2003 | Matich | 128/206.25 |
| 2006/0085883 A1* | 4/2006 | Tan et al. | 2/9 |
| 2006/0118116 A1 | 6/2006 | Porat | |
| 2007/0039620 A1* | 2/2007 | Sustello | 128/206.22 |
| 2007/0044802 A1* | 3/2007 | Horne et al. | 128/206.19 |
| 2009/0065006 A1* | 3/2009 | Patterson | 128/205.27 |
| 2009/0283096 A1* | 11/2009 | Cerbini | A41D 13/1161 |
| | | | 128/206.15 |
| 2010/0065058 A1* | 3/2010 | Ungar | A62B 18/02 |
| | | | 128/206.24 |
| 2011/0108035 A1 | 5/2011 | Samaniego | |
| 2012/0247474 A1 | 10/2012 | Torbenson | |

OTHER PUBLICATIONS

Amazon, Oct. 28, 2014, Moldex 2300N95 Disposable Particulate Respirator N95 Dust Mask, http://www.amazon.com/Moldex-2300N95-Disposable-Particulate_Respirator, pp. 1.

Walgreens, Oct. 28, 2014, 3M Particulate Respirator face mask, N95, R8511ES, http://www.walgreens.com/store/c/3m-particulate-respirator-face-mask-,-n95,-r8511es/ID=prod6152466-product, pp. 1.

* cited by examiner

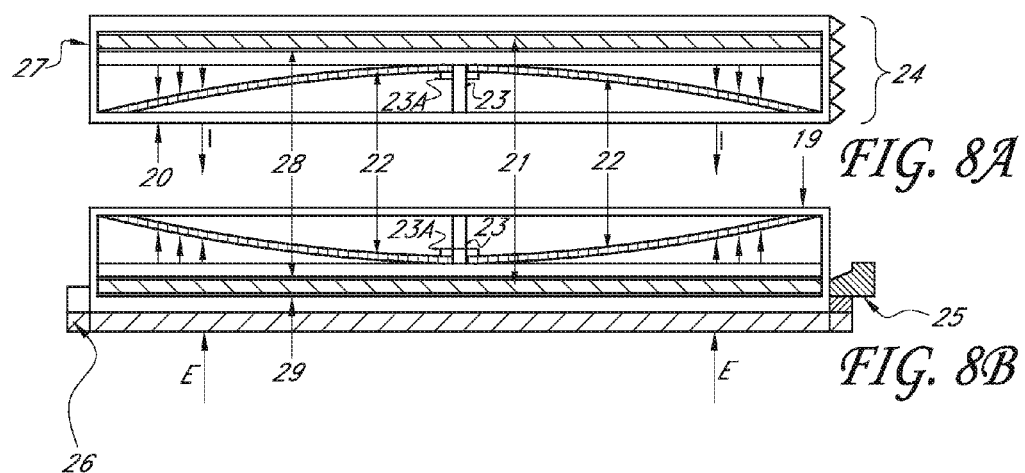
FIG. 8A
FIG. 8B
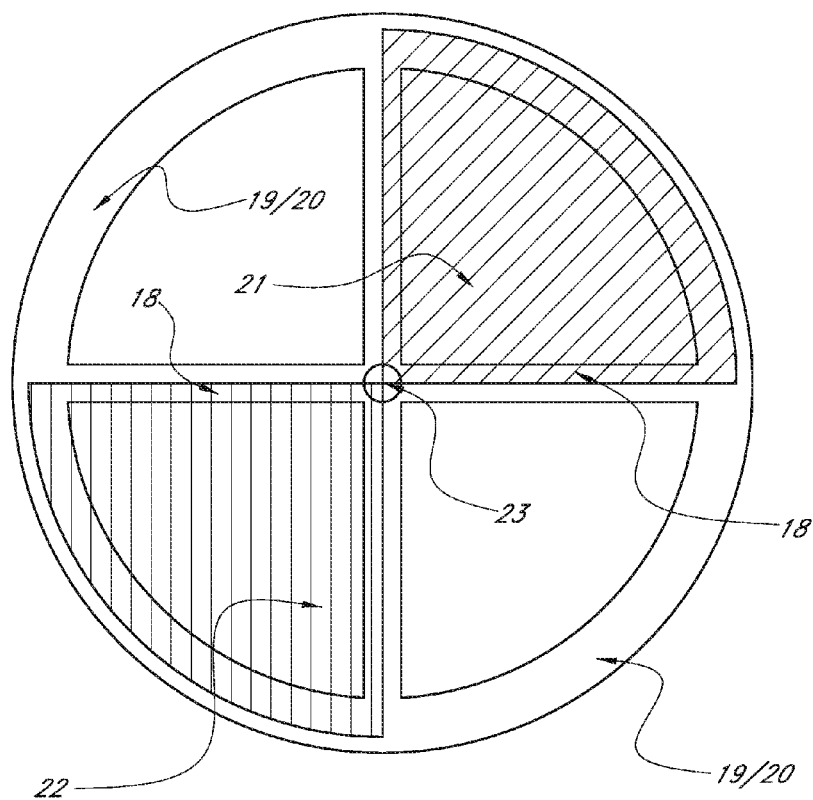
FIG. 8C

SURGICAL FACE MASK, INCLUDING REUSABLE MASKS, WITH FILTERED INHALATION AND EXHALATION VALVES

CROSS-REFERENCE TO RELATED APPLICATIONS

The present application claims priority to and is a continuation-in-part of International Patent Application No. PCT/US2010/033037, filed Apr. 29, 2010, entitled "SURGICAL FACE MASK, INCLUDING REUSABLE MASKS, WITH FILTERED INHALATION AND EXHALATION VALVES," which claims priority to U.S. Provisional Application No. 61/173,927, filed on Apr. 29, 2009 entitled FACE MASK WITH INHALATION AND EXHALATION VALVES, each of which is herein incorporated by reference in its entirety.

BACKGROUND

Face masks, such as surgical face masks, are worn by health care professionals to protect patients and wearers. Such masks can catch bacteria and viral particles shed from the wearer's mouth and nose. However, such masks are generally loose fitting with the wearer's exhalation gases flowing around the perimeter of the face mask, typically at the lower edges of the cheeks and around the chin of the wearer. Accordingly, concerns have arisen as to the effectiveness of such face masks in protecting patients (Edmiston C E Jr, et al. "Molecular epidemiology of microbial contamination in the operating room environment: Is there a risk for infection?" Surgery. (2005) 138:573-9, 579-82; and Lipp A, et al., "Disposable surgical face masks: a systematic review." Can Oper Room Nurs J. 2005 23:20-1, 24-5, 33-8; each of which is incorporated herein by reference in its entirety). In addition, such face masks may be ineffective at protecting the wearer from hazards such as surgical smoke (Alp E. et al., "Surgical smoke and infection control." Journal of Hospital Infection (2003) 62:1-5; Biggins J. et al., "The hazards of surgical smoke. Not to be sniffed at!" Br J Perioper Nurs. (2002) 12:136-8, 141-3; each of which is incorporated herein by reference in its entirety).

The human face presents a challenge for forming a seal between a face mask and the user's face. The human face is deeply contoured; moreover, the size and proportion of these contours vary widely between human faces.

Attempts have been made to better seal the perimeter of face masks. For example, U.S. Pat. No. 4,319,567 describes a thicker perimeter in the nasal bridge and lateral cheek areas, and U.S. Pat. No. 4,807,619 describes multiple layers of fibrous filter material allowing for greater facial conformity. Typically, face masks include a plastically deformable strip of metal or other material, to allow the user to customize the shape of the portion of the periphery of the mask that extends across the bridge of the nose. After loosely fitting the mask over the face, a user can plastically deform this member so as to help the mask maintain a close fit across the bridge of the nose.

Some face masks have incorporated a non-filtered exhalation valve. Such a design feature may allow exhaled gases to bypass the filter body due to less flow resistance, thereby providing greater comfort and less vapor-induced fogging. Examples of such devices include U.S. Pat. Nos. 7,188,622, 4,873,972, and 5,509,436; each of which is incorporated herein by reference in its entirety. However, none of these designs are applicable to the operating room environment, since the exhaled products are not filtered. In some embodiments herein, the teachings and apparatuses of the incorporated patents and articles may be specifically excluded.

SUMMARY

Generally, embodiments disclosed herein relate to wearable articles, including moldable face masks. Some moldable face masks can include at least an inhalation valve, an exhalation valve or preferably at least one of each. Some embodiments include methods for reducing contaminants in an inhalation and exhalation flow stream, and kits for assembling moldable face masks.

In some embodiments a face mask can include a generally cup shaped mask body that includes an opening and a recess, the recess can be shaped to receive oral and nasal features of a human face, the opening having a peripheral edge shaped to generally follow a contour of a human face extending around the nasal and oral areas; at least one moldable member (e.g., without being limited thereto, a heat-activated thermoplastic member) coupled, for example, to said peripheral edge, wherein said moldable member (e.g., heat-activated thermoplastic member) extends for at least a portion of said peripheral edge; at least two valves that include at least one exhalation valve that is disposed on the mask body and has at least one orifice that allows exhaled air to pass from an interior gas space to an exterior gas space during an exhalation; and at least one inhalation valve that is disposed on the mask body and has at least one orifice that allows inhaled air to pass from an exterior gas space to an interior gas space during an inhalation, wherein said at least two valves each include a filter element; and at least one retention member attached to said mask body. It should be noted that in some embodiments, the face mask body can include and utilize a single valve that permits the passage of air that is inhaled into or exhaled from the mask. It should also be understood that the mask body and/or elements of the mask such as filter elements or filter cavities can at least partially have a trapezoidal shape. For example, without being limited thereto, the cup shaped mask may have a trapezoidal opening, a trapezoidal recess, and/or a trapezoidal shape at the distal end.

In some embodiments, the moldable member is a material that molds to fit the contours of the face of the user. Preferably, the moldable member substantially retains it shape even when removed from the face of the wearer such that the mask has a customized fit specific for the wearer. "Substantially" retaining it shape can mean that the moldable member maintains 50%-99% of its molded shape to fit the wearer's facial contour. In some aspects, the moldable member can be a heat-activated material that is heated prior to contacting the face of the wearer. The heated material can be molded to fit the contour of the wearer's face and then substantially retains its shape to fit the wearer. The moldable member can include or be made of any other suitable material such that it can be mold to the face of the wearer and substantially retain its shape. For example, the moldable member can include a material that remains pliable until exposed to a material such as air or oxygen, upon which it will retain its molded shape. As another example, the moldable member can include a material that is activated by a catalyst (e.g., a liquid chemical, a gas chemical, etc.). In some embodiments, the moldable member (e.g., the heat-activated thermoplastic member) extends for the entirety or all of said peripheral edge. In some aspects, the moldable member (e.g., the heat-activated thermoplastic member) can extend for 50-100% or more preferably for 80-100% of the peripheral edge. In some embodiments, the moldable member (e.g., the heat-activated thermoplastic member) can be shaped to the contours of a user's face. In some embodiments, the heat-activated thermoplastic member can include, for example, ethylene vinyl acetate. In some embodiments, the moldable member (e.g., the heat-activated thermoplastic member) further can include, for example, a pressure-sensitive adhesive.

In some embodiments, the peripheral edge further can include, for example, a pressure-sensitive adhesive.

In some embodiments, the moldable member, including a heat-activated thermoplastic member, can be coupled to said peripheral edge through fenestrations in said peripheral edge. In some embodiments, moldable member (e.g., the heat-activated thermoplastic member) can be coupled to said peripheral edge with a gripping means. In some embodiments, the moldable member, e.g., the heat-activated thermoplastic member can be coupled to said peripheral edge with an adhesive agent. In some embodiments, the adhesive agent can include a KRATON® polymer or other high performance elastomer, or the like, for example.

In some embodiments, the mask body can include, for example, at least one exhalation valve opening disposed therein where said exhalation valve is located thereon. In some embodiments, the mask body can include, for example, at least one inhalation valve opening disposed therein where said inhalation valve is located thereon. In some embodiments, the mask body can include, for example, at least one exhalation valve and at least one inhalation valve. In some embodiments, the least one of said at least two valves can be replaceable. In some embodiments the inhalation and exhalation valves can be part of a single valve unit that functions as both an inhalation and exhalation valve.

In some embodiments, the filter element can be replaceable. In some embodiments, the filter element can include, for example, a fibrous material, an open-cell foam, or the like.

In some embodiments, the least one of said at least two valves can include, for example, an indicator for length of use. In some embodiments, the indicator can include, for example, soda lime or the like.

In some embodiments, the filter element of at least one of said least two valves can include a filter that can qualify as an N95 filter, for example. In some embodiments, the filter element of at least one of said least two valves can include a filter that can qualify as a N99 filter, for example. In some embodiments, the filter element of at least one of said least two valves can include a filter that can qualify as any other NIOSH rating, for example, P100 and OV-100, for example. In some embodiments a single filter element can include, for example, two or more filter pieces with different NIOSH ratings (e.g., N95, N99, P100, OV-100, etc.).

In some embodiments, the least one of said at least two valves can include a valve member, wherein said filter element extends over an exterior of said valve member. In some embodiments, the least one of said at least two valves can include a valve member, wherein said filter element extends over an interior of said valve member. In some embodiments, the least one of said at least two valves can be coupled to said mask body by a device such as, for example, a twisting flange snap fit means, a threaded twisting fit means, and a direct pressure snap fit means.

In some embodiments, the at least one retention member can include, for example, an elastomeric member coupled to said mask body. The retention member further can include, for example, and a hook and loop strap coupled to said elastomeric member.

In some embodiments, a face mask described herein can further include at least one viso-elastic member disposed on the interior of said mask body at a location that can be aligned with a position such as the nasal bridge of a user, and the lower chin of a user, for example.

In some embodiments, a face mask described herein can include, for example, a styrene-based polymer, an isopyrene polymer, a low density polyethylene copolymer, and/or mixtures thereof, and the like.

In some embodiments, a face mask described herein can further include a generally cup shaped insert that includes an opening and a recess, the recess shaped to receive oral and nasal features of a human face, and said insert can be adapted to be inserted into said mask body. In some embodiments, the insert further can include, for example, at least one exhalation valve opening disposed therein where said exhalation valve is located thereon, and at least one inhalation valve opening disposed therein where said inhalation valve is located thereon. In some aspects, at least one single valve that has the ability to filter both inhaled and exhaled gas may be used. In some embodiments, the insert can be replaceable. The insert can be comprised of a material that provides filtration, for example, an N95 or higher filter material (e.g., N99, P100, OV-100, etc.). The insert can include a cloth material, a moisture absorbing material, and the like.

Some face masks described herein can include a generally cup shaped mask body that includes, for example, an opening and a recess, the recess shaped to receive oral and nasal features of a human face, the opening having a peripheral edge shaped to generally follow a contour of a human face extending around the nasal and oral areas; a moldable member (e.g., a heat-activated thermoplastic member or other member as described herein) coupled to said peripheral edge, wherein said moldable member extends for at least a portion of said peripheral edge; and at least one retention member attached to said mask body. In some aspects the moldable member can extend continuously over the entire length of the peripheral edge. In some aspects the member can extend discontinuously over the length of the peripheral edge. In some aspects, the moldable member can extend over 40%-100% of the peripheral edge of the mask body. In some aspects, the mask can include more than one moldable member (e.g., a separate layer inside of or adjacent to the outer layer) or one moldable member and a separate elastomeric member adjacent to, inside of or near the heat-activated thermoplastic member. The masks further can include any of the other devices and features described herein. The masks can specifically exclude one or more of the other features or apparatus described above and elsewhere herein. It should also be understood that the mask body and/or elements of the mask such as filter elements or filter cavities can at least partially have a trapezoidal shape. For example, without being limited thereto, the cup shaped mask may have a trapezoidal opening or a trapezoidal shape at the distal end.

Some embodiments described herein can include methods for removing contaminants from an inhale flow stream and exhale flow stream of a user. Such methods can include obtaining a face mask described above and elsewhere herein and contacting it with the face of user thereby removing contaminants that are exhaled from the user and filtering contaminates in air inhaled by the user. Further methods can include obtaining a face mask described herein; molding a moldable member such as a heat-activated thermoplastic member or any other member as described herein, to a contour extending around the nasal and oral areas of said user's face; and placing the mask over at least the user's oral and nasal features, such that a substantial portion of the inhaled air (e.g., 50%-100%, preferably 80%-100%, for example) passes through at least one inhalation valve, and a substantial portion of the exhaled air (e.g., 50%-100%, preferably 80%-100%, for example) passes through at least one exhalation valve. In some aspects, the inhalation and exhalation valves can include at least one valve where they are the same. In some embodiments, the molding can include, for example, heating a heat-activated thermoplastic member; and contacting the face of said user with said heat-activated thermoplastic member such that said heat-activated thermoplastic member contours a region extending around the nasal and oral areas of said user's face. It should be noted that the moldable member can be activated by other means (catalyst or other chemical material such as air) depending upon the particular material that is selected. In some embodiments, the peripheral edge further can include, for example, a pressure-sensitive adhesive, such that said pressure-sensitive adhesive contacts a contour extending around the nasal and oral areas of said user's face.

Some embodiments described herein include face mask kits, for example, for assembling or replacing parts of a face mask. The kits can include, for example, one or more of the following: a generally cup shaped mask body that includes an opening and a recess, the recess shaped to receive oral and nasal features of a human face, the opening having a peripheral edge shaped to generally follow a contour of a human face extending around the nasal and oral areas; a moldable member as described herein (e.g., a heat-activated thermoplastic member, etc.) coupled to said peripheral edge, wherein said moldable member extends for at least a portion of said peripheral edge; at least two valves comprising at least one exhalation valve and at least one inhalation valve, wherein said at least two valves each comprise a filter element; at least generally cup shaped insert comprising an opening and a recess, the recess shaped to receive oral and nasal features of a human face, and said insert is adapted to be inserted into said mask body; at least one retention member; and optionally, instructions for assembling the face mask. In some aspects the device can include a single apparatus that functions as both an exhalation and inhalation valve. In some embodiments, a kit further can include a pressure-sensitive adhesive or other suitable adhesive. It should also be understood that the mask body and/or elements of the mask such as filter elements or filter cavities can at least partially have a trapezoidal shape. For example, without being limited thereto, the cup shaped mask may have a trapezoidal opening or a trapezoidal shape at the distal end.

Some embodiments relate to reusable surgical face masks of a generally cup shaped design. It should also be understood that the mask body and/or elements of the mask such as filter elements or filter cavities can at least partially have a trapezoidal shape. For example, without being limited thereto, the cup shaped mask may have a trapezoidal opening or a trapezoidal shape at the distal end. The masks can be constructed of soft plastic copolymer such as, but not limited to, LDPE. The masks can include, for example, a mask body that includes one or more receptacles; at least one reusable, replaceable or both reusable and replaceable filtered exhalation valve, wherein the at least one exhalation valve is configured to fit into a receptacle in the mask body; at least one reusable, replaceable or both reusable and replaceable filtered inhalation valve wherein the at least one inhalation valve is configured to fit into a receptacle in the mask body; a moldable border (e.g., a heat-activated border) around the entire perimeter of the mask that can molded to the face of a user; and a retention or strap system for securing the mask to the face of the user. For example, the retention system can include a passive/active adjustable strap system (PAASS) for securing the mask to the user's head.

For example, the border can include a heat activated material which upon heat activation can conform to the face of a user. The heat activated border can include, for example, a thermoplastic polymer, such as for example, one or more of EVA, PO or a combination thereof.

In some aspects, the border may be secured to the perimeter section of the mask body by the use of oval spaced fenestrations around said perimeter of the mask body. The border may secured to the perimeter section of the mask body, for example, by using a soft malleable metal strip, or strips, which is/are incorporated into the mask body perimeter. The border may be secured to the mask body by using a strip or strips of a thermoplastic elastomeric compound which is molded into the mask perimeter section. In some preferred aspects, without being limited thereto, the border can include a thermoplastic elastomeric material.

The mask can include, for example, one or more, preferably at least two exhalation valves. The exhalation valves may be for example multi-use detachable replaceable (MDR) exhalation valves that are secured to the outer sides of the mask. In some aspects, at least one such valve (e.g., MDR inhalation valve) may be secured to the central portion of the mask by utilizing one or more of a twisting flange snap fit; a threaded twisting fit; or a direct pressure snap fit. In some aspects a single exhalation valve can be used, while in others, two or more may be used.

The mask body can include, for example, a unique passive active adjustable strap system (PAASS) for attaching the mask to the user's head. The PAASS system may include, for example, an elastomeric coupler attached to the mask housing by small bridges molded into the mask housing; and hook and loop straps which attach to the elastomeric sections and secure to their respective opposite ends.

The mask body may include, for example, a styrene-based thermoplastic elastomeric compound. In some aspects, the mask body may include, for example, an isopyrene polymer. The mask body may include, for example, any combination of LDPE, styrene-based polymers, isopyrene based polymers and/or other polymers and/or copolymers of thermoplastic elastomeric composition, and the like.

Some embodiments relate to an MDR inhalation/exhalation valve assembly, which assembly can include, for example, one or more of a valve housing with two chambers, one enclosing a thin disc valve supported by a valve post and retaining disc molded into the valve housing; a filter element of NIOSH N95 qualification (or other qualification, e.g., N99, P100, OV-100, etc.); a filter element of NIOSH N99 qualification (or other qualification, e.g., N95, P100, OV-100, etc.); and an open cross bridged housing on both sides for air flow through the valve and filter. Such valves assemblies can be utilized with any of the masks described herein, if desired. The valve assembly further may include, for example, an outer perimeter molded flange for a twisting snap fit securing action. The valve assembly may include a threaded perimeter for a twisting screw-in securing action to secure the valve into a mask valve receiving region.

Some embodiments relate to valve assemblies as described herein that are configured to directly snap fit into a mask housing. The valve can be reusable and/or disposable. The valve assembly further may include an indicator for $CO_2$ absorption, for example. The indicator can include, for example, soda lime crystals or any other suitable material. The filter element of the assembly can be replaced separately from the valve assembly itself, for example.

Some embodiments relate to masks that utilize at least one valve assembly as described herein. The at least one valve assembly may be molded into the mask body as a permanent part of the mask body. The outer housing cover over the valves may include, for example, one or more of: a molded disc cover with space beneath by which air flow is allowed across the valve assembly; a molded disc with cross sections to allow air flow across the valve assembly; cross sections directly molded into the mask housing flush to the secured valves; and the like. The masks further may include a replaceable adhesive backed strip of material attachable on the inside of the mask body. said material can include, for example: (a) synthetic elastomeric foam; (b) synthetic felt; (c) any such material designed for similar purposes; or (d) combinations of any of (a)-(d). The material may be attached, for example, at either the inside of the mask body at the nasal bridge and/or along the inside of the mask body at the lower chin section.

Some embodiments relate to masks that include a body, wherein the body comprises a heat-activated thermoplastic copolymer EVA custom moldable border section. The mask further can include, for example, a PAASS.

The foregoing is a summary and thus contains, by necessity, simplifications, generalization, and omissions of detail; consequently, those skilled in the art will appreciate that the summary is illustrative only and is not intended to be in any way limiting. Other aspects, features, and advantages of the devices and/or processes and/or other subject matter described herein will become apparent in the teachings set forth herein. The summary is provided to introduce a selection of concepts in a simplified form that are further described below in the Detailed Description. This summary is not intended to identify key features or essential features of the claimed subject matter, nor is it intended to be used as an aid in determining the scope of the claimed subject matter.

BRIEF DESCRIPTION OF THE DRAWINGS

The foregoing and other features of the present disclosure will become more fully apparent from the following description and appended claims, taken in conjunction with the accompanying drawings. Understanding that these drawings depict only several embodiments in accordance with the disclosure and are not to be considered limiting of its scope, the disclosure will be described with additional specificity and detail through use of the accompanying drawings.

FIG. 8A shows a transverse view of an inhalation valve. FIG. 8B shows a transverse view of an exhalation valve. FIG. 8C shows a frontal view of a valve.

DETAILED DESCRIPTION

Figure 1:
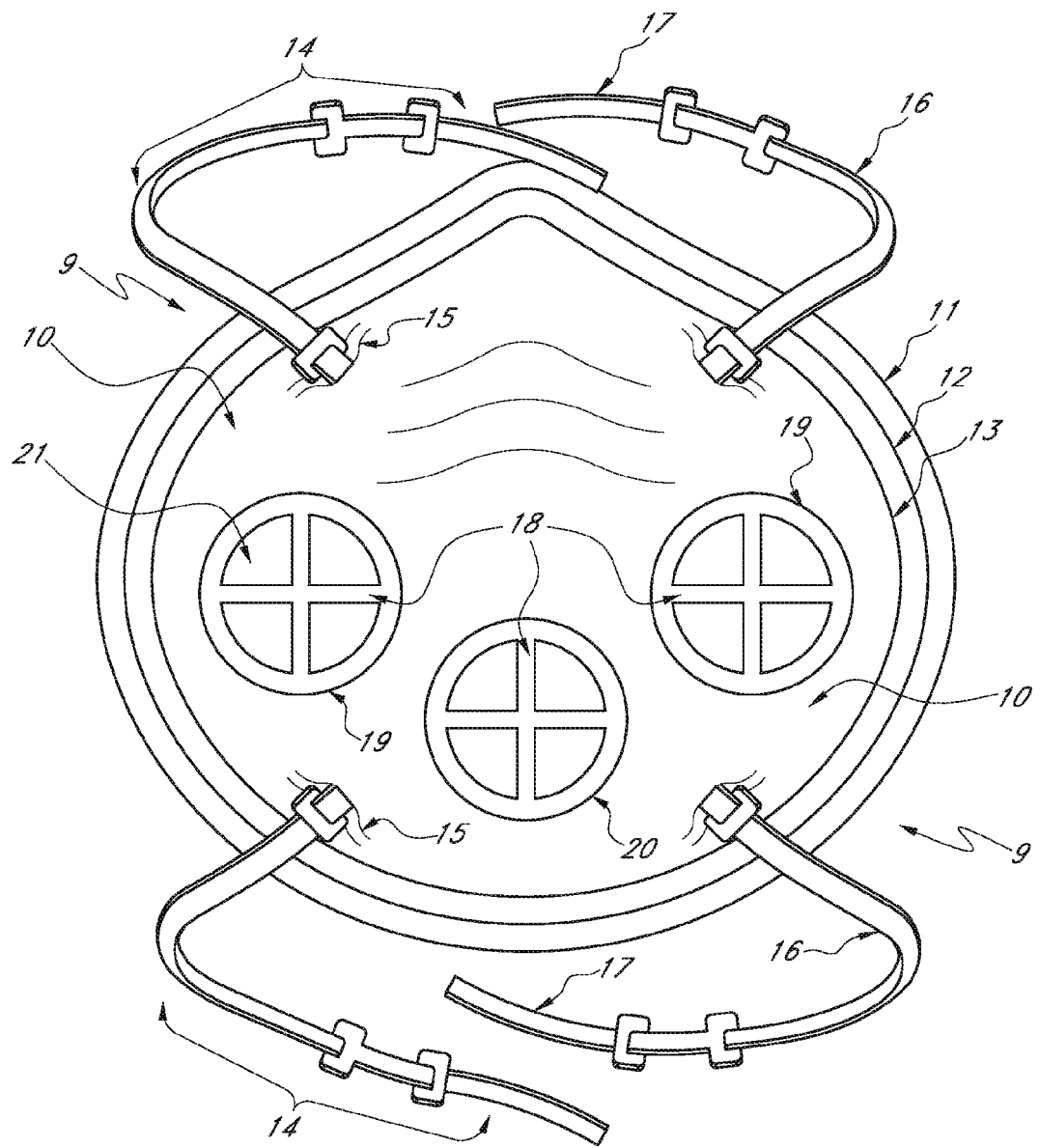
FIG. 1 shows a frontal view of a face mask.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and make part of this disclosure.

Generally, embodiments relate to face masks, for example that can be used in a surgical field, but not limited to such use. The masks can include a custom fitting reusable (if desired) mask body, one or more multiuse filtered valves (replaceable if desired), and an adjustable detachable strap system, for example.

The mask body can be composed of, for example, a cup-shaped shell. Preferably, the cup-shaped shell can be made of a semi-rigid generally cup-shaped shell. It should also be understood that the mask shell can at least partially have a trapezoidal shape. Any suitable material can be used. For example, the body can be made of a plastic copolymer, including a soft plastic copolymer. In some aspects the shell can be made of a material that can be cleaned and/or sterilized. The mask border perimeter can include a moldable material (e.g., a moldable member) that permits at least a portion of the mask (e.g., the perimeter border or any other part that is desired to be custom fitted) to be custom fitted to the individual's face. For example, the mask can include a heat activated material which upon heating can be custom fitted to the individual's facial contour in contact with the mask. In some aspects the moldable material can include a material that can be molded to the contours of the user's face and that will substantially retain its shape. In some aspects, the term "substantially retain" can mean that it will maintain about 50%-100% of its molded shape for at least 1 day to about 1 month, for example. The material can be, for example, heat activated, a material that is catalyzed by a catalyst, a material that becomes active upon exposure to air or some other gas, and any other suitable material that can be molded and then retain its molded shape. The semi rigid mask body can include at least one filtered inhalation valve, for example, centrally located and one or more filtered exhalation valves, for example, peripherally located. These valves can be of a multiuse detachable replaceable design. In some aspects a single device can be used that can function to filter both inhalation and exhalation air. Preferably, the valve or valves have an airflow capacity that permits all of the exhaled and inhaled air to pass through the valves rather than through the perimeter of the mask, when the mask is secured to the head of a user. In some aspects, one or more of the components described above and elsewhere herein can be specifically excluded from some embodiments.

The mask body can be held to the wearer by an attachment mechanism. Any suitable mechanism can be utilized. The mechanism can include an elastic material and non-elastic material. The attachment mechanism can include clips, buttons, clamps, hook and loop (e.g., Velcro®), the like, etc. Preferably, the attachment mechanism can be a two piece (or more) partially elastic passive/active adjustable/detachable strap system. In some aspects the masks can include a colored straps. For example, the straps can come in a variety of colors, and can be used as a means of applying unique identifiers for the different categories of operating room personnel, for example. The colors can also be used as size, source, or ownership identifiers, for example. The colors can be used to personalize the masks, which can be reused. The various functions of the different colored straps can be particularly useful or important in certain settings, such as surgical settings.

The masks, mask components, other mask features, and methods described herein described herein, can provide greater protection to both the user and those around the user. In the surgical setting, the described technology can provide protection for the wearer of the mask, as well as, those in the surgical field. Furthermore, in some aspects many of the components of the masks can be reused, while others can be replaced, resulting in masks that provide greater comfort, safety and significant cost savings, compared to masks of the prior art.

Some embodiments generally relate to wearable articles including face masks, in particular, including moldable face masks. Some moldable face masks can include, for example, at least one inhalation valve. Some moldable face masks can include, for example, at least one exhalation valve. Some moldable face masks can include, for example, both at least one inhalation valve and at least on exhalation valve. In some aspects a single valve can be used that function to filter both inhalation and exhalation gases. Some embodiments relate to components of the masks and mask systems described herein. Further aspects include methods for reducing contaminants in an inhalation and exhalation flow stream, and methods and kits for assembling the face masks and components thereof described herein.

The face masks and mask components described herein can be used in applications where it is desirable to reduce contaminants flowing to and from a wearer's nose and mouth during exhalation and inhalation. Such contaminants can include, for example, bacteria, viruses, surgical smoke, and the like. As used herein, "wearer" and "user" can be synonymous. Generally, the face masks described herein may be used by health care professionals or any other user who desires to avoid contamination or who desires to avoid spreading a contaminant.

Some face masks described herein can include a generally cup shaped mask body comprising an opening and a recess, the recess shaped to receive oral and nasal features of a human face, the opening having a peripheral edge shaped to generally follow a contour of a human face extending around the nasal and oral areas; a moldable member or sealing member coupled to said peripheral edge, wherein said member extends for at least a portion of said peripheral edge; one or more valves, for example, an exhalation valve that is disposed on the mask body and has at least one orifice that allows exhaled air to pass from an interior gas space to an exterior gas space during an exhalation; or at least one inhalation valve that is disposed on the mask body and has at least one orifice that allows inhaled air to pass from an exterior gas space to an interior gas space during an inhalation, wherein said valves include a filter element; and at least one retention member attached to said mask body. In some aspects, the inhalation and exhalation valves can be the same or part of a single valve system. More than one of the valves can be utilized if desired. The valves can be replaceable in some aspects. It should also be understood that the mask body and/or elements of the mask such as filter elements or filter cavities can at least partially have a trapezoidal shape. For example, without being limited thereto, the cup shaped mask may have a trapezoidal opening or a trapezoidal shape at the distal end.

In some embodiments, the moldable or sealing member can include one or more of a heat-activated thermoplastic member, a pressure sensitive adhesive, other adhesive or the like. The moldable or sealing member can include a material that can be molded and which can substantially retain its molded shape. That material can be a heat-activated material, a gas activated material, a catalyst activated material, or the like, for example. The moldable or sealing member can be coupled to said peripheral edge, wherein said member extends for at least a portion of said peripheral edge. For example, it can extend over 40% to 100% of the edge.

Preferably, the mask can include at least two valves, including at least one exhalation valve that is disposed on the mask body and has at least one orifice that allows exhaled air to pass from an interior gas space to an exterior gas space during an exhalation; and at least one inhalation valve that is disposed on the mask body and has at least one orifice that allows inhaled air to pass from an exterior gas space to an interior gas space during an inhalation, wherein said at least two valves each comprise a filter element.

The face masks described herein can be molded to the contours surrounding the nose and mouth of a particular user's face. In some embodiments, a moldable member as described herein can be used. For example, the masks can utilize a heat-activated thermoplastic member extending around the peripheral edge of a face mask can be made pliable and molded to the contours of a user's face. Because contours of human faces can vary enormously, this feature can be particularly advantageous to produce a tight fit at the edges of the face mask and reduce the amount of air flowing around the periphery of the face mask.

A heat-activated thermoplastic member can be made pliable, for example, by exposing it to heat, such as a hot or boiling liquid, a warm or hot gas, or energy such as microwaves. It can be molded, for example, by placing it on the user's face and applying pressure thereby causing the member to mold to the contour of the user's face. Examples of such heat-activated thermoplastics include ethylene vinyl acetate (EVA), polyolefin materials (PO), and the like.

In some embodiments, a face mask further may include a pressure sensitive adhesive on the peripheral edge of the mask such that a seal can be made between the periphery of the face mask and the user's face, for example. Generally, any pressure sensitive adhesive may be used. Preferably, the pressure sensitive adhesive does not cause irritation to human skin or is so aggressively adhesive that it causes pain to the user when removed from the skin. It also can be desirable that the adhesive is selected such that the adhesive does not leave a substantial amount of an adhesive residue on the surface of the skin of the user, when mask is removed by the user after use. For example, it is preferred that the adhesive leave no residue, or less than 10% residue for example. Particularly suitable pressure sensitive adhesive materials are disclosed in U.S. Pat. Nos. 6,213,993 and 6,620,143, the entire disclosure of each is incorporated herein by reference. Other suitable adhesives are disclosed in U.S. Pat. No. 5,618,281, the entire disclosure of which is incorporated herein by reference. Other known body adhesives, such as those described in U.S. Pat. No. 6,316,524, which is hereby incorporated in its entirety, may also be used. Other examples of pressure sensitive adhesives include, hydrogels, hydrocolloids, acrylics based adhesives, and rubber based adhesives, such as Kraton® based adhesives/elastomers.

In addition, some of the face masks described herein can include at least one inhalation valve and at least one exhalation valve. Such valves can include filter elements that remove contaminants from the inhalation and exhalation air flow of a user. It is envisioned that the proportion of the inhalation air flow and/or exhalation air flow that will pass through the filter elements of the inhalation and exhalation valves will be at least 30%, 40%, 50%, 60%, 70%, 80%, 90%, 95%, 99%, and 100% or any value in between. In some embodiments, the inhalation valves and exhalation valves can be reusable. In some aspects the valves can be replaceable. In some embodiments, filter elements of the inhalation valves and exhalation valves are reusable and/or replaceable. In some aspects one or more single valves can be used that are capable of filtering both inhaled and exhaled gases.

In some embodiments, the face masks described herein can include a passive-active adjustable strap system (PAASS) to hold the mask in place over a user's nose and mouth. A PAASS can include retention members. The retention members can include, for example, a two piece adjustable head strap that allows the user to set the tension specific to their facial cranial anatomy, while allowing for a degree of elasticity in the headbands.

Face masks can further include a disposable generally cup shaped insert. The insert can include an opening and a recess, the recess shaped to receive oral and nasal features of a human face, where the insert is adapted to be inserted into the body of the mask, for example, within the perimeter of the shell and the moldable material (e.g., EVA, PO, adhesive, etc.). In some embodiments, the inserts further can include one or more holes or openings to permit gas or airflow through the inhalation and exhalation valves. For example, the holes or openings can be positioned to line up with the inhalation and/or exhalation valve(s). The inserts can include attachment mechanisms to secure the inserts to the interior of the mask body or to secure the inserts in an appropriate position relative to the valves. For example, the inserts can include openings with O-rings that can fit onto or around the one or more valves. The inserts can be of any suitable material. For example, the inserts can include a filter material, such as a fibrous material, or an open-cell foam. In some aspects, the inserts can include an N95 or higher material (e.g., N99, P100, OV-100, etc.). The inserts can include a material that is moisture absorbing, which provides comfort, etc. It should also be understood that the mask body and/or elements of the mask such as filter elements or filter cavities can at least partially have a trapezoidal shape. For example, without being limited thereto, the cup shaped mask may have a trapezoidal opening or a trapezoidal shape at the distal end.

In addition to the face masks described herein, methods for reducing or removing contaminants from an inhale flow stream and exhale flow stream of a user are described. As used herein "removing" can refer to removing, blocking or filtering at least a portion, for example at least a portion of the contaminants in airflow. At least a portion can mean, in some aspects, removing 50%-100% of contaminants (or any value there between), preferably 90%-100% of the contaminants. Some such methods can include, for example, obtaining a face mask described herein and placing the mask over at least the user's oral and nasal features. Also, some such methods can include, for example, obtaining a face mask described herein; molding a moldable member (e.g., without limitation a heat-activated thermoplastic member) to a contour extending around the nasal and oral areas of said user's face; and placing the mask over at least the user's oral and nasal features, such that a substantial portion (e.g., 50-100% or any amount there between) of the inhaled air passes through said at least one inhalation valve, and a substantial portion (e.g., 50-100% or any amount there between) of the exhaled air passes through said at least one exhalation valve.

Also described herein are kits for assembling or replacing components of a face mask. Such kits can include, for example, one or more of: a generally cup shaped mask body that includes an opening and a recess, the recess shaped to receive oral and nasal features of a human face, the opening having a peripheral edge shaped to generally follow a contour of a human face extending around the nasal and oral areas; malleable or moldable member coupled to said peripheral edge, wherein said member extends for at least a portion of said peripheral edge (e.g., 40%-100% or any value in between); one or more valves such as an exhalation valve or an inhalation valve; at least generally cup shaped insert that includes an opening and a recess, the recess shaped to receive oral and nasal features of a human face, and wherein insert is adapted to be inserted into said mask body; at least one retention member; and instructions for assembling the face mask. Some kits can include a heat-activated thermoplastic member coupled to said peripheral edge, wherein said heat-activated thermoplastic member extends for at least a portion of said peripheral edge. Some kits can include a pressure-sensitive adhesive extending for at least a portion of the peripheral edge. In some aspects the kids can include both a moldable member and a pressure-sensitive member. In some aspects, the kits can include at least two valves comprising at least one exhalation valve and at least one inhalation valve, wherein said at least two valves each include a filter element. In some aspects, the inhalation and exhalation valve(s) can be the same. It should also be understood that the mask body and/or elements of the mask such as filter elements or filter cavities can at least partially have a trapezoidal shape. For example, without being limited thereto, the cup shaped mask may have a trapezoidal opening or a trapezoidal shape at the distal end.

Some embodiments relate to methods of making or custom fitting a mask to a user. The methods can include any of the materials and or methods described herein. The methods can specifically exclude one or more of the materials, components and/or methods described herein. For example, the methods can include providing a mask shell (e.g., as described herein), which shell includes a moldable member, along with instructions for molding the mask to conform substantially, at least around a portion of the mask perimeter, to the face of a user. The mask shell further can include one or more holes or openings that can receive one or more valves for inhalation and/or exhalation. The shell can include a suitable attachment mechanism including the mechanisms described herein. The attachment mechanism can include colored components, for example, to designate the type of personnel, the size, and/or the type of use that may be appropriate for the mask. By appropriate use, for example, one color may designate use in a particular clean room. Some straps may be of a color that designates suitability for use in a clean room (e.g., manufacturing environment), an operating room, etc. The methods may include the use of any other components as described herein.

Figure 2:
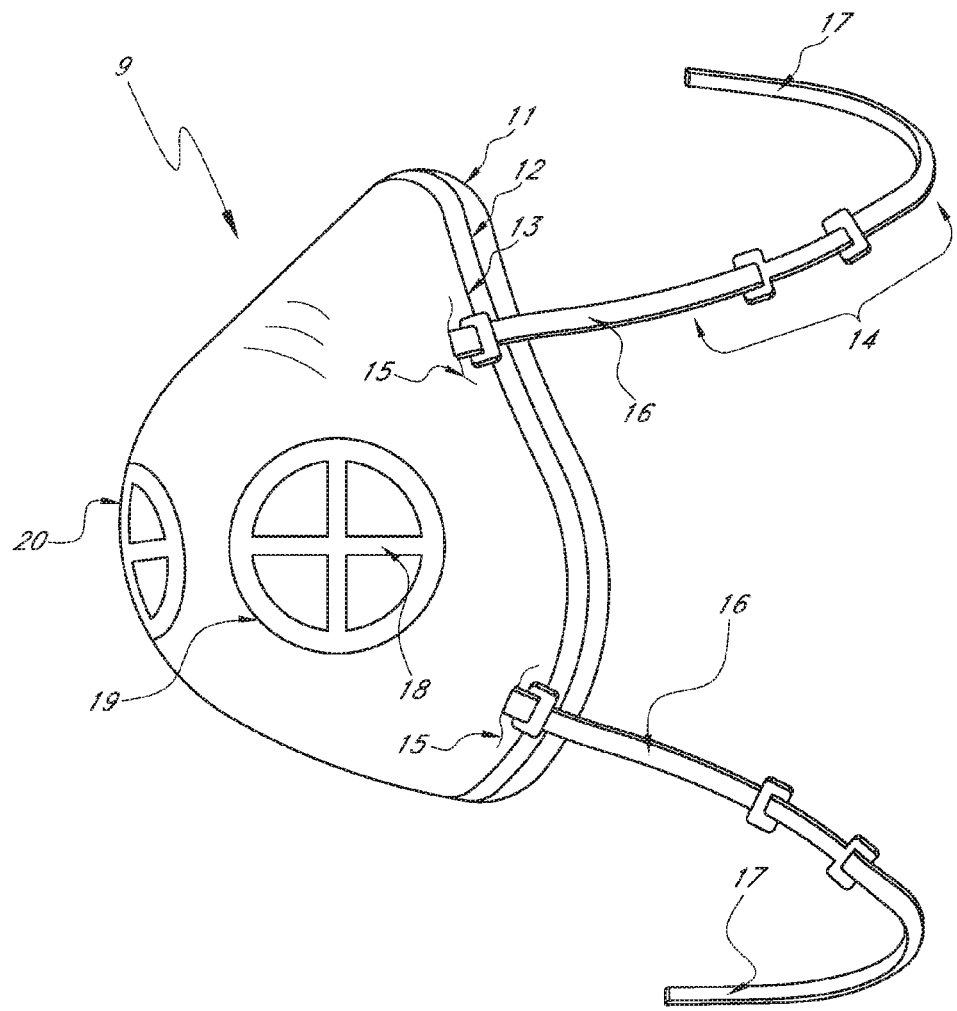
FIG. 2 shows a side view of a face mask.
Figure 3A:
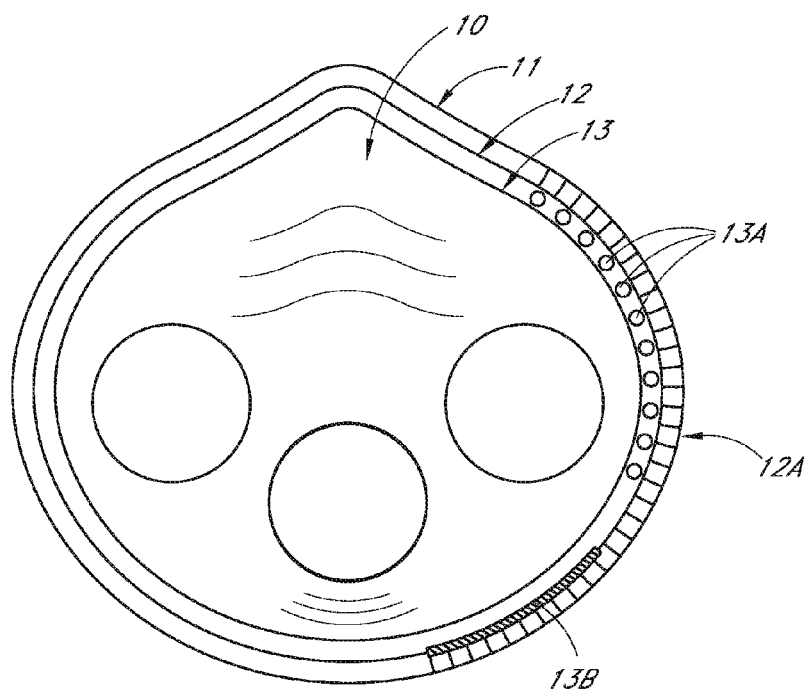
FIG. 3A shows a frontal view of a face mask.
Figure 3B:
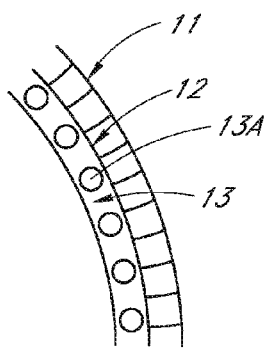
FIG. 3B shows a close up view of the mask perimeter section, perimeter edge, and moldable border.
Figure 3C:
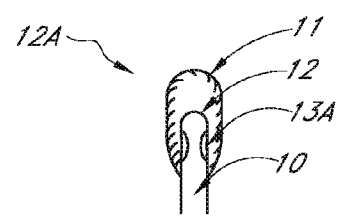
FIG. 3C shows a close up view of perimeter edge of the mask perimeter section, perimeter edge, and moldable border at a point midway through a fenestration.
Figure 3D:
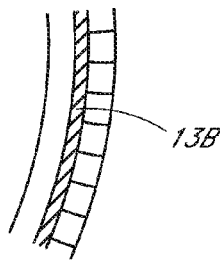
FIG. 3D shows a close up view of a mask perimeter section, perimeter edge, and moldable border.

Referring to FIGS. 1 and 2, in some embodiments a face mask 9 can include, for example, a generally cup shaped mask body 10 with an opening and a recess, the recess shaped to receive oral and nasal features of a human face, such as the bridge of the nose, cheeks, mid to lower mandible of the jaw, and under the chin. The mask body can have a peripheral edge 12 shaped to generally follow a contour of a human face extending around the nasal and oral areas. The peripheral edge 12 can be adjacent to a peripheral section 13 of the mask body.

In some embodiments, the mask body can include a moldable member 11 as described herein, for example, a heat-activated thermoplastic member. The moldable member 11 may be referred to herein as a heat-activated thermoplastic member. However, it should be understood that other types of moldable members are contemplated for use, but are not necessarily specifically mentioned in connection with the drawings. Thus, whenever a heat-activated thermoplastic member is mentioned, it should be appreciated that other types of moldable members can be substituted or used in addition to the heat-activated member. In some embodiments, the heat-activated thermoplastic member 11 can be coupled to the peripheral edge 12 of the mask body. The heat-activated thermoplastic member 11 can extend along at least a portion of the peripheral edge 12. As used herein, "at least a portion" can refer to between about 1% and 100% of the peripheral edge, including at least 1%, 5%, 10%, 20%, 30%, 40%, 50%, 60%, 70%, 80%, 90%, 95%, 99%, and 100%. In some embodiments, the heat-activated thermoplastic member can extend along the entirety of the peripheral edge.

The mask body 10 can include a thermoplastic polymer and/or an elastomeric polymer, for example, a polyethylene, polystyrene, a low density polyethylene (LDPE), an isopyrene polymer, mixtures thereof, and the like. The peripheral section 13 and peripheral edge 12 can each include or be made of the same material(s) or different materials as the mask body 10. Generally, the mask body can include a non-porous material.

In some embodiments, the heat-activated thermoplastic member 11 can include a heat-activated thermoplastic compound, for example, ethylene vinyl acetate (EVA) or polyolefin (PO). EVA is approved for oral use by the Food and Drug Administration (FDA). The thermoplastic member 11 can allow for the mask to custom fit the specific facial contours of the user.

The face mask 9 as depicted includes valves 19, 20. The valves can include at least one inhalation valve 20 that is disposed on the mask body and has at least one orifice that allows inhaled air to pass from an exterior gas space to an interior gas space during an inhalation, and at least one exhalation valve 19 that is disposed on the mask body and has at least one orifice that allows exhaled air to pass from an interior gas space to an exterior gas space during an exhalation. The face mask depicted in FIG. 1 includes a single inhalation valve 20 and two exhalation valves 19. Without being limited thereto, the inhalation valve 20 can be disposed within a central location of the mask body 10. Such a central location may be a path of least resistance for inhaled air flow during use of the mask. Without being limited thereto, the exhalation valves 19 can be disposed at the outer sides of the mask body 10. The depicted valves 19, 20 include a filter 21 within the valve apparatus. The filter 21 can be of a type, for example, that meets the National Institute of Occupational Safety and Health (NIOSH) standards, including the N 95 standards (95% filtering efficiency of all non-oil based particles as defined by the NIOSH). It should also be noted that in some embodiments one or more valves that filter both inhalation and exhalation gas may be utilized.

The masks 9 of FIGS. 1 and 2 include a passive-active adjustable strap system (PAASS) 14 attached to the mask body 10. It should be noted that other types of retention or strap systems may be used to secure the mask to the face of the user. The depicted system 14 can include an elastomeric coupler 16 attached to the mask body 10 at raised bridges 15 in the mask body. A hook-and-loop fastener strip 17, for example, made of nylon or polyester, can be coupled to the elastomeric coupler 16. Although not depicted, the straps can be at least partially color coded as discussed elsewhere herein.

Figure 4A:
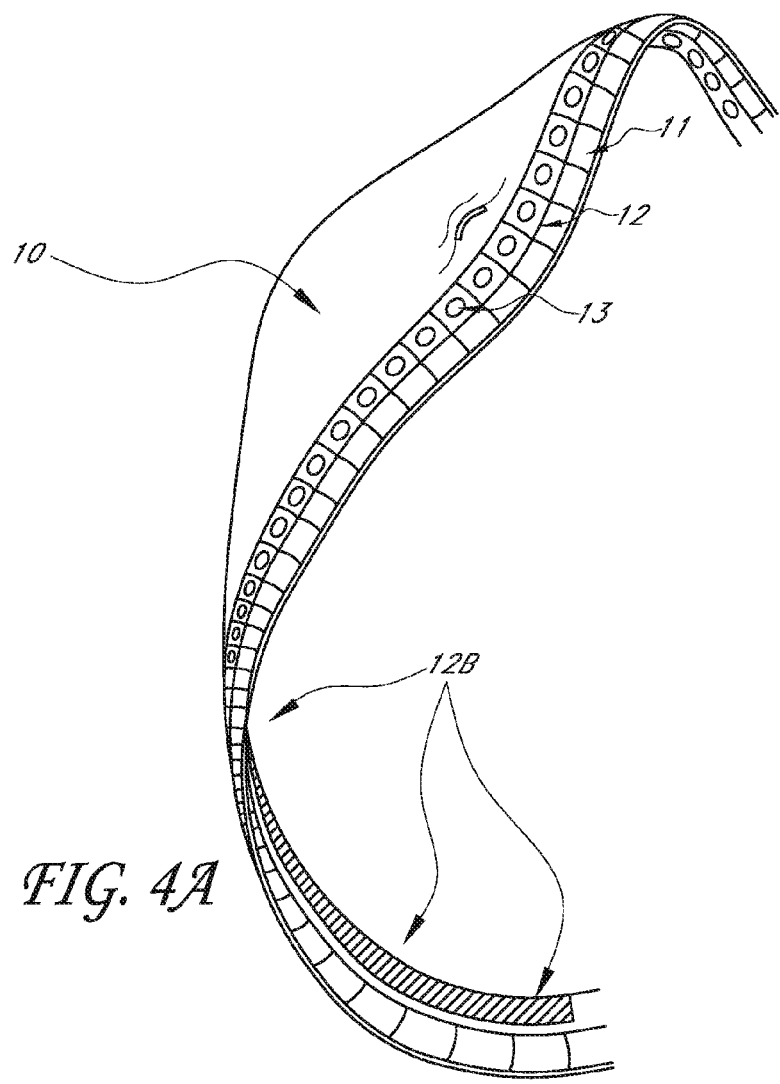
FIG. 4A shows an inside view angle of a face mask.
Figure 4B:
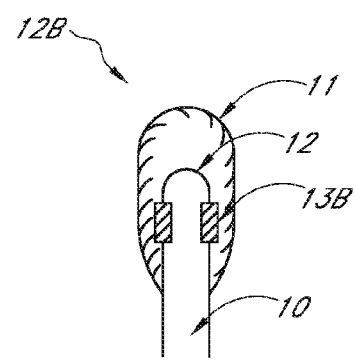
FIG. 4B shows a close up view of the mask perimeter section, perimeter edge, and moldable border.

FIGS. 3 and 4 depict a mask body 10 with moldable border 11 (e.g., EVA) attached to the perimeter edge 12 via an overlapping of the border 11 around perimeter edge 12 along the mask body perimeter section 13. The attachment can be accomplished by a variety of methods. Two such methods of attachments along the mask perimeter section 13 are illustrated. In one embodiment, the heat-activated thermoplastic member 11 can be coupled to the mask body 10 through a plurality of oval fenestrations or holes 13a located in the peripheral section 13. FIG. 3 illustrates oval fenestrations 13a spaced along the perimeter section 13 allowing passage of the thermoplastic material (e.g., EVA) from both sides of border 11 through the oval fenestrations 13a in the perimeter section 13. Feature 12a illustrates a cross section of the perimeter edge 12 showing thermoplastic material border 11 filling around and through the fenestrations 13a as depicted in perimeter section 13 and thus sealed to perimeter edge 12. While oval fenestrations are depicted, it should be understood that fenestrations or holes of any appropriate shape can be utilized, for example, circular, square, rectangular, etc. The fenestrations or holes further can have an opening that is smaller than the interior of the hole or fenestration or that can include a portion that extends under the surface of the material. Such a configuration can help to "anchor" the moldable member.

An alternative border 11 attachment using semi-pliable strips 13b is shown in FIG. 3 whereby strips of a malleable softened metal, such as for example aluminum, are used around the perimeter section 13. This attachment allows for a gripping effect of the thermoplastic border 11.

FIG. 4 depicts an example cross section 12b of edge 12 with the metal strips 13b along each side of perimeter section 13 and border 11 thus sealed around the metal strips 13b and thus sealed to perimeter edge 12.

In another embodiment, a moldable member, such as a heat-activated thermoplastic member 11, can be coupled to a mask body 10 by an adhesive. Examples of such adhesives include low resilience high compression elastomeric compounds Such compounds may include any of the styrene based category, and/or those of the polyisoprene category. One example of such compounds is a thermoplastic rubber marketed as KRATON® IR, by GLS Corp, 833 Ridgeview Drive, McHenry, Ill. 60050. This compound is FDA approved and is also injection moldable. It also adheres to other copolymers including EVA and LDPE, but has a significantly higher softening point than either EVA or LDPE. It should be noted that such a coupling of EVA to KRATON® is used successfully in athletic protective devices, one example of which is U.S. Pat. No. 5,339,832 to Kittelsen et al., which is incorporated herein by reference in its entirety. However, many such thermoplastic elastomeric compounds exist, and any of those with appropriate thermoplastic properties and FDA approval can be utilized with the devices and methods described herein.

Figure 5:
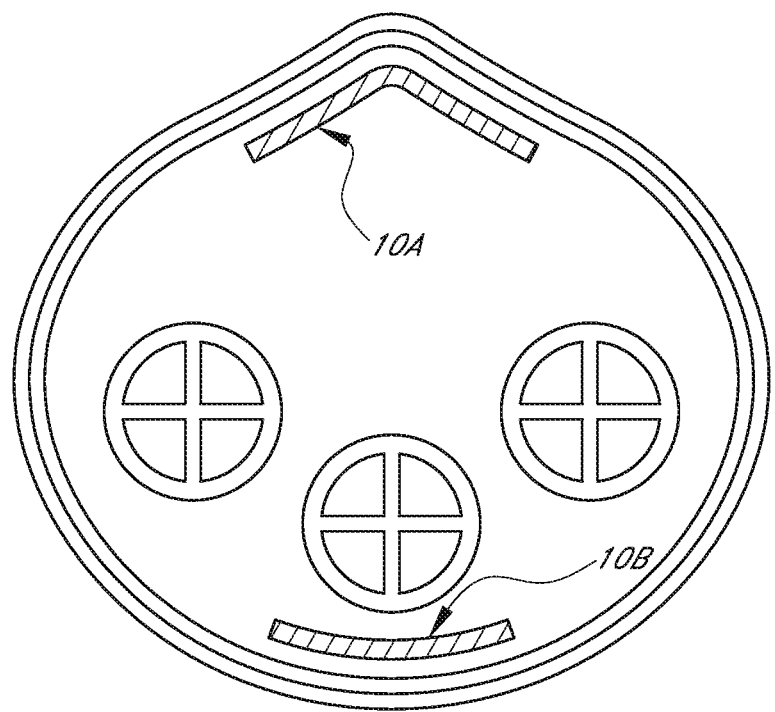
FIG. 5 shows an interior view of a face mask and a transverse view of a face mask.

FIG. 5 illustrates another embodiment whereby at locations 10a and 10b the user can, if so desired, attach an additional devices, for example, adhesive backed strips of soft synthetic composition for additional comfort and/or moisture control. Attachment point 10a is for additional comfort on the inside of the nasal bridge, if so desired. Attachment point 10b, under the user's chin, can be used for additional comfort if so desired and as an additional moisture absorptive layer. It should be noted that although FIG. 5 shows two specific attachment point locations, any location can be selected according the comfort and/or moisture control needs of the user. Any synthetic soft material can be used for these adhesive backed strips. One example is a synthetic felt, another example being elastomeric foam. Many examples of such materials for such purposes exist and easily can be selected in consideration of the instant disclosure. Preferably, a material safe for use in contact with the human face can be used. These strips can be supplied with the device in initial packaging or kits, and can be replaced as desired.

Figure 6:
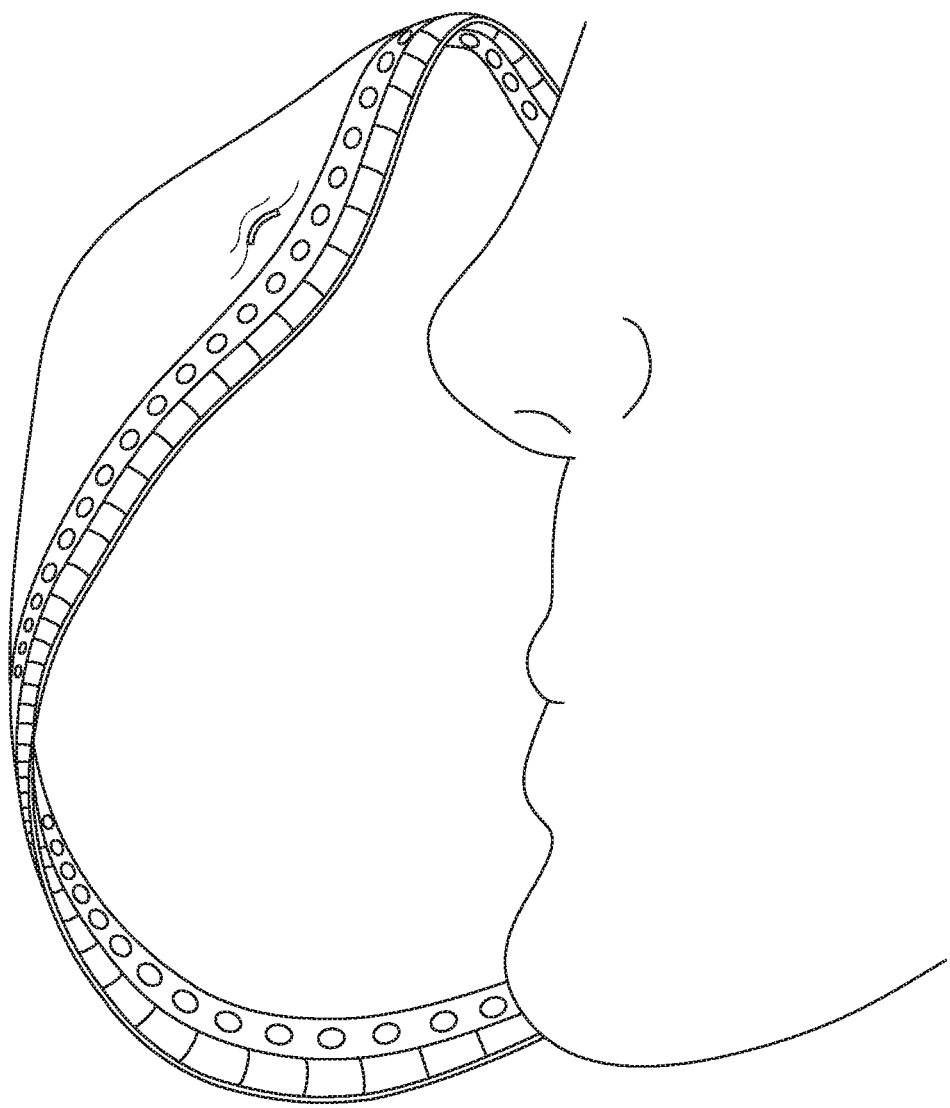
FIG. 6 shows a schematic view of a user's face and an interior view of a face mask.

Referring to FIG. 6, the heat-activated thermoplastic member 11 of a moldable face mask described herein can be molded to a contour extending around the nasal and oral areas of a user's face. It should be noted that initially the mask may come at least partially disassembled. For example, the mask can be taken out of the packaging by the user without the filtered valve inserts secured and without the PAASS attached. The mask body 10 with the heat-activated border can be activated by placing the perimeter edge with the border of the mask body in hot water, for example, water at a temperature of @140 F, for a period of time sufficient to soften the heat-activated border material. The mask is removed from the hot water, cooled slightly to prevent burning the user, and placed with mild pressure to the user's face such that the softened heat-activated border comes into a comfortable position that would be the standard position for the mask while in use. In this fashion, the perimeter border can conform in a manner unique to each individual's facial contours. Once fitted, the user can cool the mask by any suitable method including for example by running cold water over the mask body including the perimeter edge to allow re-hardening of the heat-activated border material. Even in the "hardened" state, materials such as EVA provide a smooth soft surface for contact with the facial anatomy, and in this state EVA is FDA approved for use inside the human mouth under athletic contact conditions. In some embodiments other forms of heat can be used if desired or in order to accommodate the particular heat-activated material. For example, steam or microwave heat can be utilized. It further should be noted that the user may to first apply, if so desired, any commercially available facial lotion to the facial skin prior to fitting so as to provide comfort from any thermal effect during the fitting process.

Figure 7A:
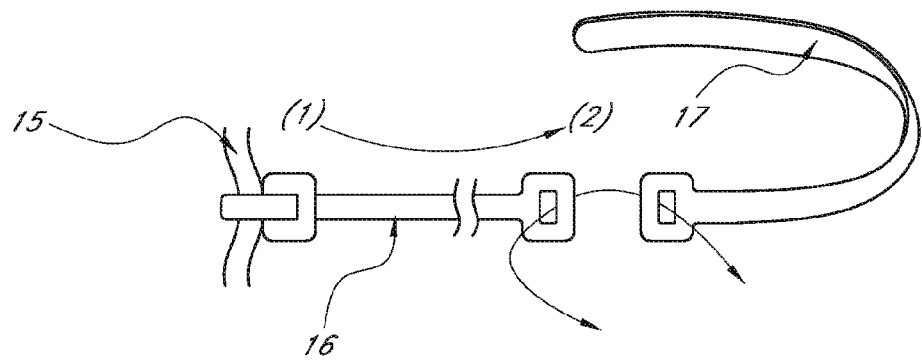
FIG. 7A shows a retention member of a face mask.
Figure 7B:
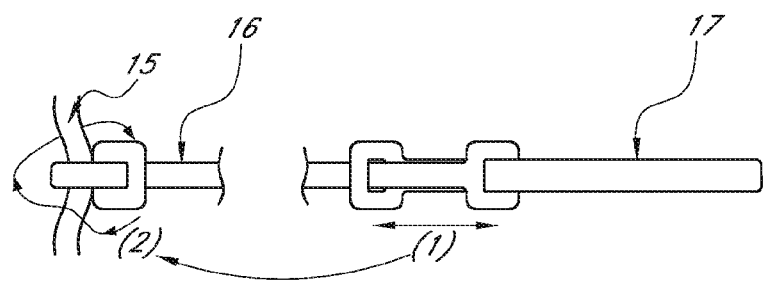
FIG 7B shows the retention member of the face mask attached in a first fastened position.
Figure 7C:
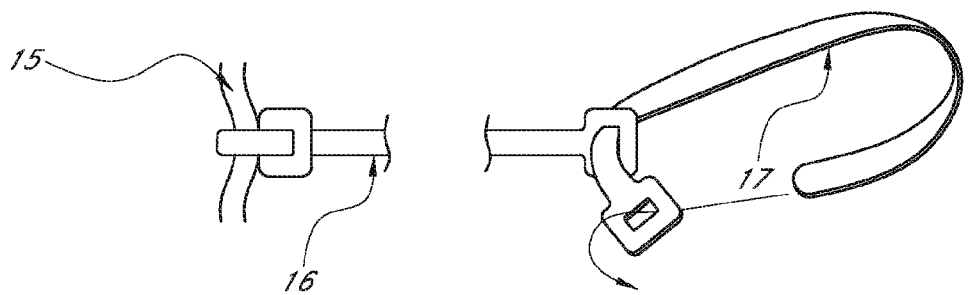
FIG. 7C shows the retention member of the face mask in a second fastened position.

Referring to FIG. 7, some face masks described herein can include a retention system or member for attachment of the mask to the face of the user. FIG. 7 illustrates an example of a PAASS for attachment of the mask body to the face of a user. In FIG. 7 the PAASS 14 is comprised of an elastomeric section 16 which attaches to, and can detach from, mask body 10 by a looping action at four bridges 15 that are part of the body 10. A hook and loop strap 17 can be coupled to the elastomeric member 16 by a variety of methods. In FIG. 7A, the elastomeric coupler section 16 is attached to points 15 first, and section 17 then looped to section 16. Alternatively, as in FIG. 7B, the hook and loop fastener strip 17 can be attached first to section 16, and the coupled PAASS 14 then attached to mask body 10 and bridge points 15.

In one embodiment, the hook and loop section 17 can come in a variety of colors, and can be used as a means of applying unique identifiers for the different categories of operating room personnel.

FIG. 8 illustrates the design of a multiuse disposable exhalation/inhalation valve 19, 20. Referring to FIG. 8, some face masks described herein can include one or more valves. In some preferred aspects the devices can include at least two valves, namely, at least one inhalation valve 20, and at least one exhalation valve 19. An exhalation valve can include at least one orifice that allows exhaled air to pass from an interior gas space to an exterior gas space during an exhalation. An inhalation valve has at least one orifice that allows inhaled air to pass from an exterior gas space to an interior gas space during an inhalation. The valve 19, 20 is illustrated with respect to the positioning in mask body, for example, mask body 10 of FIGS. 1 and 2.

A valve can include a filter element 21 that removes particulate matter from the air flow through the filter element. The orientation of the filter 21 and the valve 22 action against valve chamber floor 28 dictates the direction of air flow: air flow "I" indicating inhalation orientation and air flow "E" indicating exhalation orientation. The filter element 21 can include any material suitable material, such as for example, a fibrous material or an open cell foam. In some embodiments, the filter element can qualify as a N95 filter, namely, a N95 rating of National Institute for Occupational Safety and Health (NIOSH). In some embodiments, the filter element can qualify as a N99 filter, namely, a N99 rating of NIOSH. In some embodiments, the filter element can qualify as a N100 filter, namely, a N100 rating of NIOSH. Any other suitable filter element can be included, for example, one with an OV-100 rating. In some embodiments, a valve, a filter element, or any component of the valve can be replaceable.

Valve housing 19, 20 can include two chambers, one containing filter 21 and the opposite chamber enclosing valve 22 supported on valve post 23 with disc support 23a. Air flow is permitted through the valve by the open outer housing 19, 20 with cross structures, for example, cross structure 18 shown in FIGS. 1 and 8. Center support of the cross structures 18 is via valve post 23. In another embodiment, the valve housing 19, 20 can incorporate a detachable cover 26, allowing for replacement only of filter 21.

The valves can be designed to be replaceable at scheduled intervals to be determined individually depending upon areas of use, for example, areas of use within a healthcare facility. In certain embodiments, a valve can include an indicator for the length of time the face mask has been used by a user. In such embodiments, the indicator can include, for example, crystals sensitive to repeated exposure to gases such as $CO_2$ for example, soda lime crystals. In some aspects, the crystals can be placed within the valve housing 19, 20 filter chamber of filter 21.

Figure 9A:
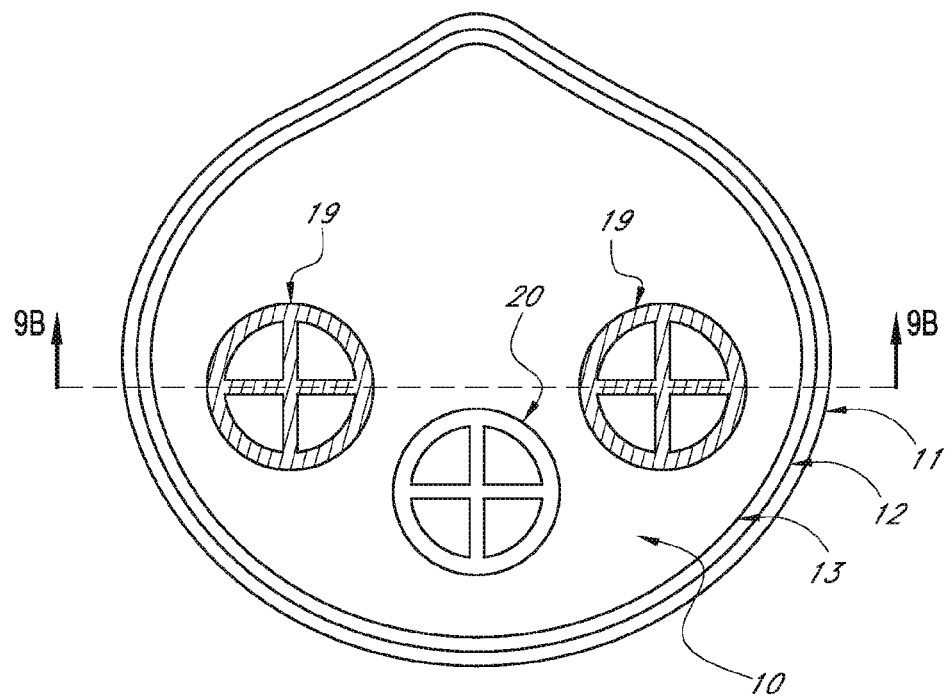
FIG. 9A shows an interior view of a face mask.
Figure 9B:
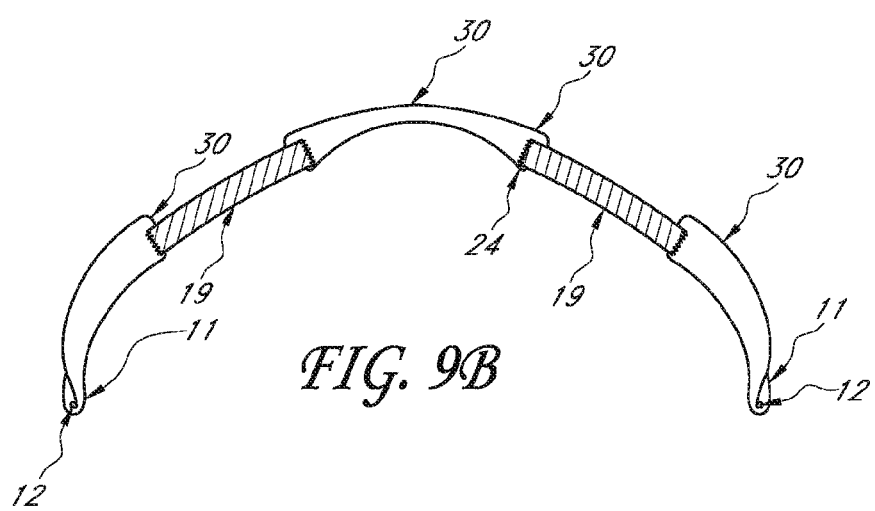
FIG. 9B shows a cross-sectional view of the face mask of FIG. 9A.

Referring to FIG. 9, some of the face masks described herein can include at least two openings in the mask body 10 to receive at least two valves 19, 20. The peripheral edge of an opening 30 can include a thickened region of the mask body 10. These outlets 30 incorporate a thickened housing recess 31 molded into the mask body 10 allowing space within which valves 19, 20 can be secured.

Figure 10A:
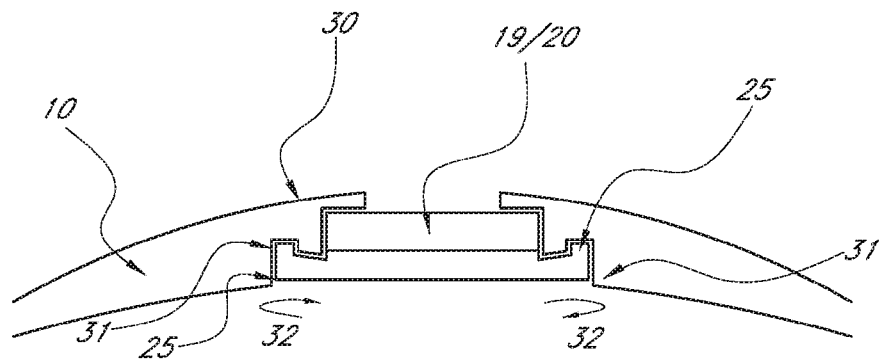
FIGS. 10A-C show three embodiments of a valve positioned in the mask body of a face mask.
Figure 10B:
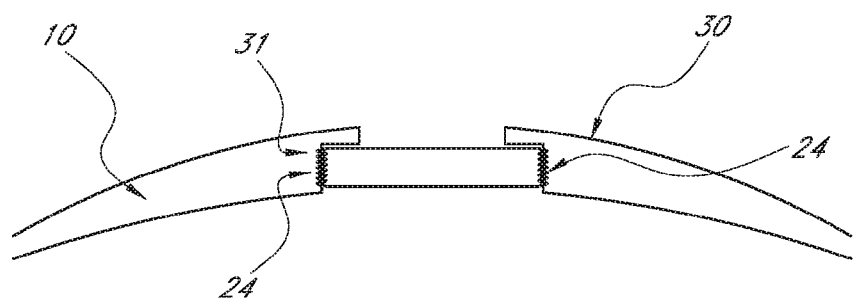
Figure 10C:
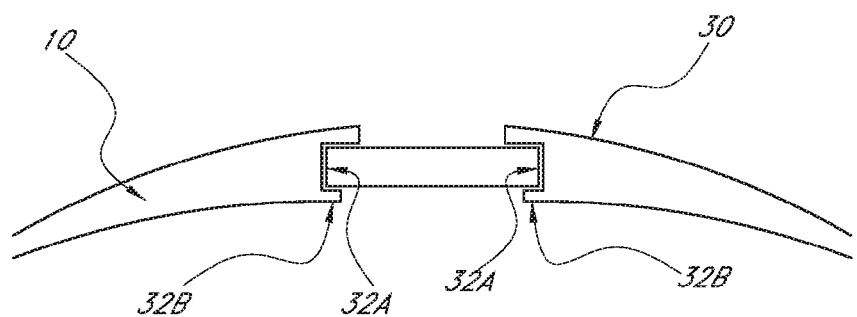

FIG. 10 illustrates three examples by which valves 19, 20 can be secured into mask housing 10 at outlets 30. Referring to FIG. 10, the thickened region of the mask body 30 can provide a surface to attach a valve 19, 20 in the mask body 10. A valve can be attached to a mask body by a variety of methods. In one embodiment, a valve can be attached to a mask body the peripheral edge of an opening 30 by a locking flange system. The locking flange system can include a valve with a flange 25 and receiving groove 31 in the peripheral edge of an opening 30. This can allows a twisting snap fit action 32 into the housing recess 31.

In another embodiment, a valve 19, 20 can include a circumference, where the circumference is threaded 24. The threaded circumference of the valve can be received by a threaded edge 31 of the peripheral edge of an opening 30. A screwing action can seat a valve 19, 20 into the threaded edge 31.

In another embodiment, a valve 19, 20 snap fits with mild pressure 32*a* directly into a recess 32*b* in the peripheral edge of an opening 30. In some aspects, the inner perimeter of recess 31 is sectioned out in locations around the perimeter 32*b*.

In another embodiment, the valve housing can incorporate a snap fit or threaded twist-on cover 26 over the filter chamber such that the filter 21 itself can be replaced independent of replacing the valve assembly.

Figure 11A:
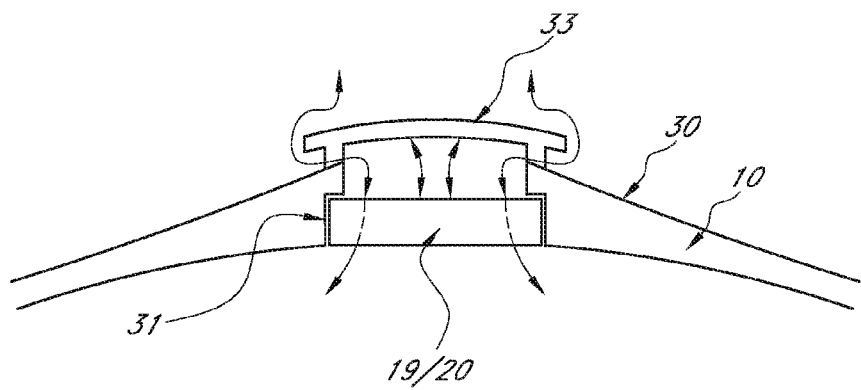
FIGS. 11A-C show three embodiments of a valve positioned in the mask body of a face mask body.
Figure 11B:
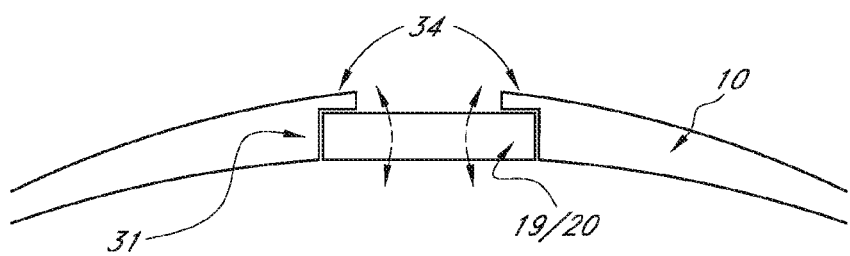
Figure 11C:
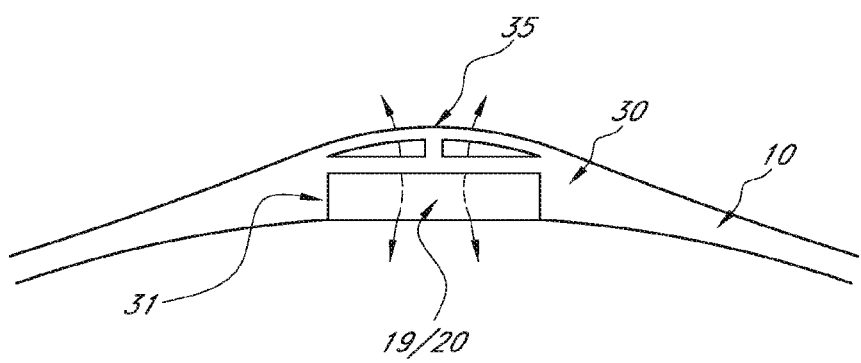

Referring to FIG. 11, some face masks described herein can comprise a valve, where the valve includes a cover. In one embodiment, a valve 19, 20 can include a cover 33 on the exterior surface of the valve. The cover 33 can be molded such that an air flow can pass under the cover and through the filter element 21. It will be understood, that such a cover can be associated with either an exhalation valve or inhalation valve, for example, depending upon valve orientation. In another embodiment, the peripheral edge of an opening 30 can be molded with a perimeter lip 34. The perimeter lip 34 can secure the valve 19, 20 from any outward slippage, while allowing ample surface area for airflow. In another embodiment, the outer housing outlet 31 incorporates molded cross bars 35 directly over the valves 19, 20. In another embodiment, the valves 19, 20 can be molded into the mask body 10 in outlet locations 30 whereby the filters 21 alone can be replaced.

It will be understood that any combination of valves described herein can be used with the face masks described herein. Also, with the instant disclosure, one of skill in the art can select other types of valves for use with the masks.

Another embodiment can incorporate fixation points in the upper outer portions of mask body, for example, body 10 of FIG. 1 to which a disposable face shield, many examples of which exist, can be attached.

Figure 12:
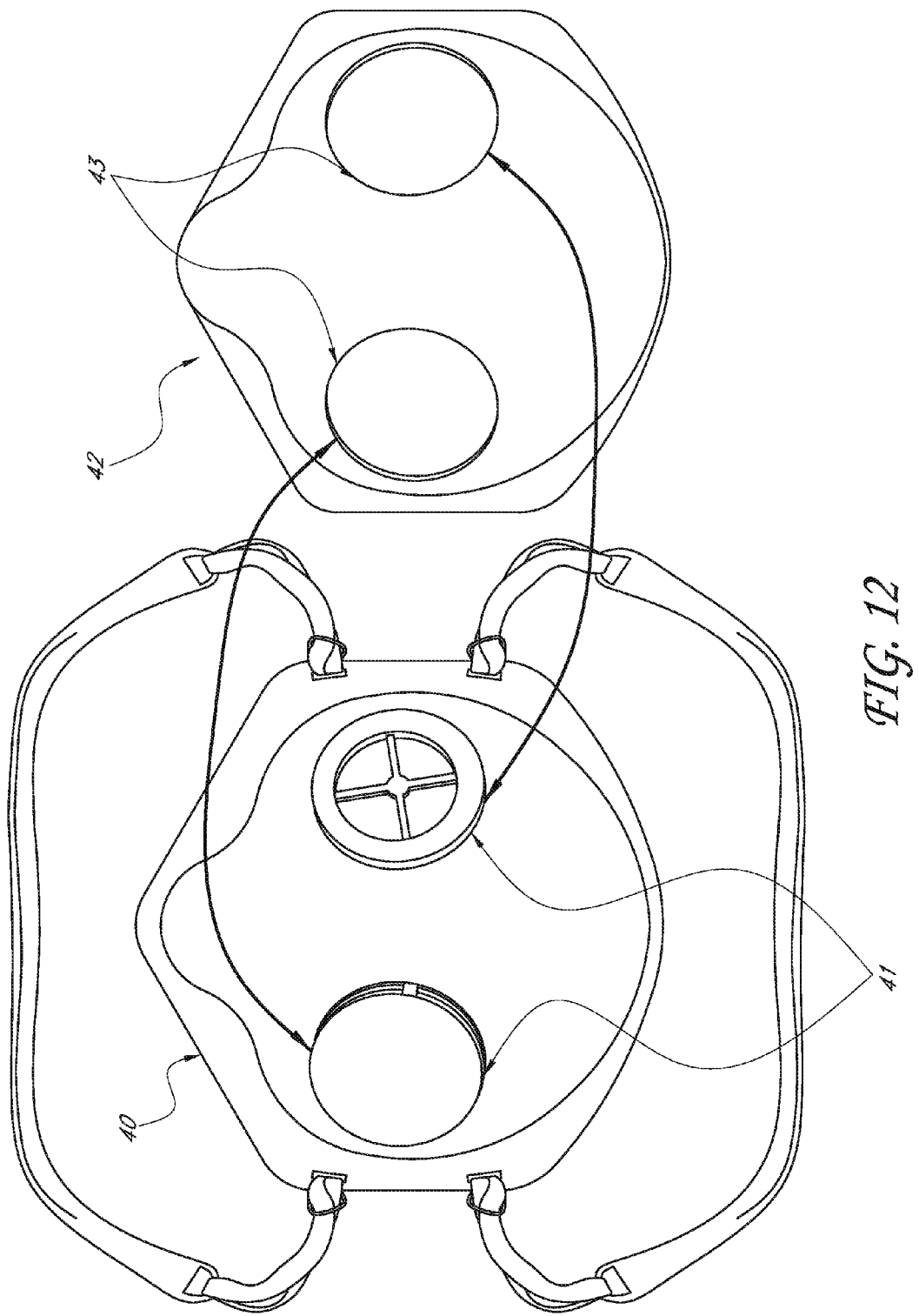
FIG. 12 shows a frontal view of some examples of components of a face mask system.
Figure 13:
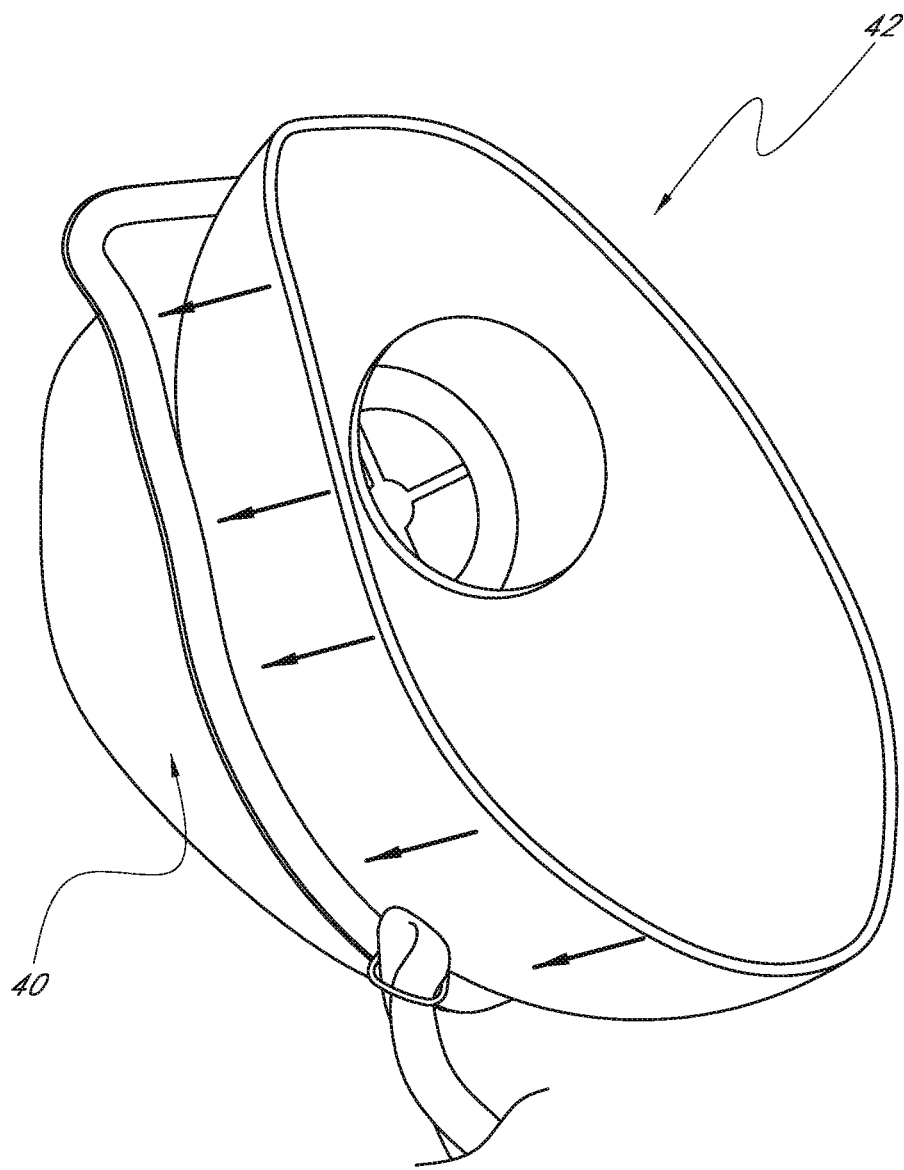
FIG. 13 shows a side view of a face mask system illustrating the insertion of an insert into a mask body.
Figure 14:
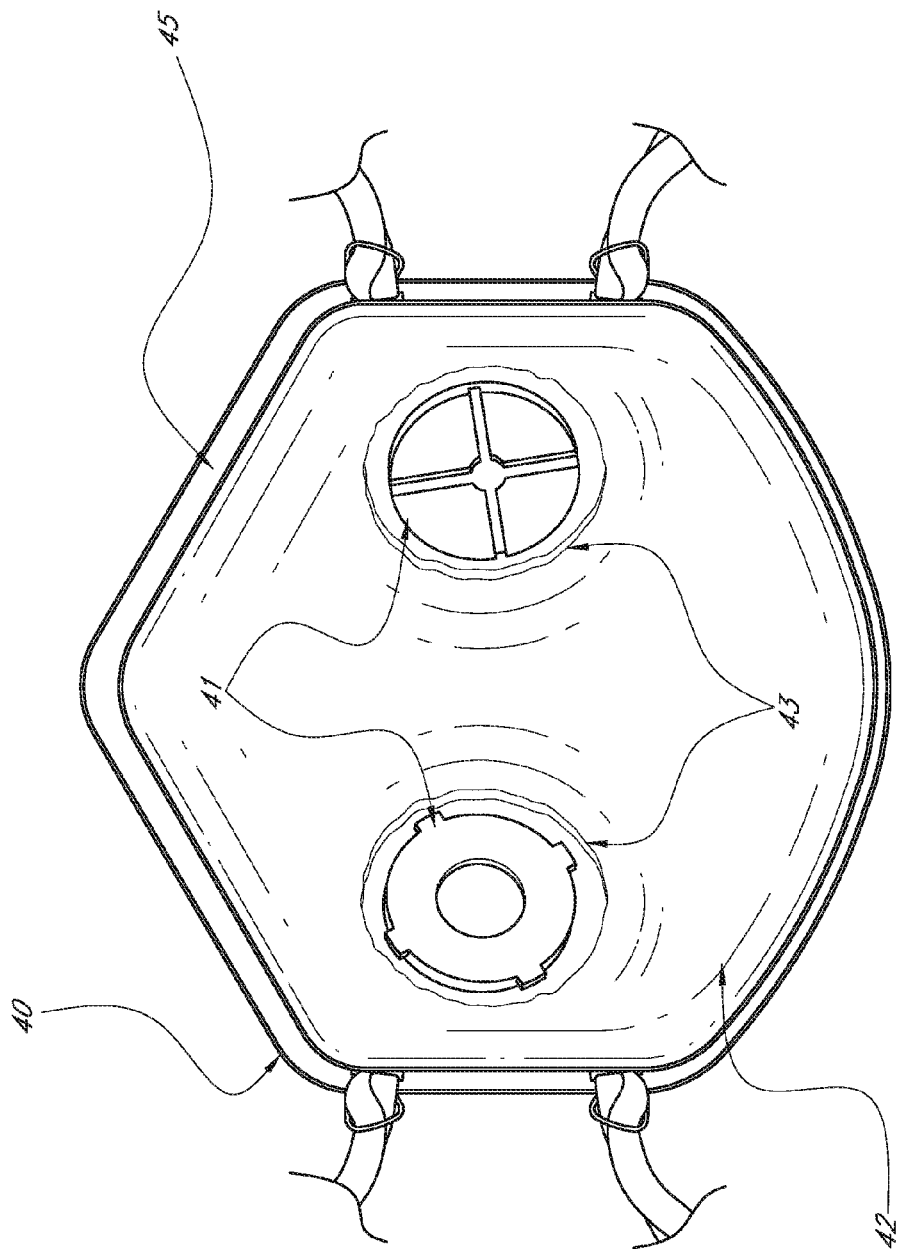
FIG. 14 shows a rear view of a face mask with an insert inserted into a mask body.

FIG. 12 is a frontal view that depicts an example face mask system according to one embodiment. The depicted system includes a mask body 40, which includes two valves 41 within the body. Also depicted is an insert 42. The depicted insert 42 includes two openings 43, which are optional. Inserts are described more fully elsewhere herein. The depiction illustrates the insert 42 prior to its insertion into the inner side of the mask body 40. The long arrows illustrate the respective openings 43 and the valves 41 that will line up once the insert 42 is inserted into the mask body 40. FIG. 13 is a side or perspective view that illustrates the insertion of an insert 42 into the cavity section of a mask body 40. FIG. 14 depicts a rear view of a mask system with an insert 42 inserted into the mask body 40. The openings 43 are aligned with the valves 41. It should be noted that in some embodiments the insert 42 can include "O" rings around the openings 43. The O rings can be configured to permit the insert 42 to press fit over the valve 41 housings in the mask body 40. In the depicted example, the insert 42 is an N95+ filter (other filter elements can be used as well, e.g., N99, P100, OV-100, etc.). FIG. 14 also depicts a border 45. In the depicted system the border 45 includes a moldable gel rim. As depicted, the moldable gel rim includes a heat-activated thermoplastic material around the perimeter of the mask body 40. The insert 42 can include an edge overlap that is inside of the thermoplastic material. In some aspects, insert 42 can include an edge overlap that includes thinner strip at the edge that conforms over the thermoplastic gel rim.

Some embodiments relate to methods of making or assembling face masks as described herein. In some embodiments, a face mask can be assembled by a user. In some embodiments, a heat-activated thermoplastic member attached to the mask body, without valves or retention members, can be held such that the heat-activated thermoplastic member is placed into a hot water bath at 140° F. After a brief cooling period, without the heat-activated thermoplastic member hardening, the mask can be held to the user's face in the position of intended use. With a gentle pressure the heat-activated thermoplastic member will contour itself to the user's unique facial perimeter anatomy. After a few seconds of application to the face, the mask body can be briefly bathed in cold water to allow for hardening of the heat-activated thermoplastic member. Even in the "hardened" state, the heat-activated thermoplastic member can provide a smooth soft surface for contact with the facial anatomy. It should be understood that the heat-activated material can be replaced or supplemented with a material that is "activated" in some other way. For example, the moldable material can be one that is activated by a catalyst or one that is reactive with a gas a chemical, or the like. Once activated, the material can molded as described above, by applying it to the face of the user with gentle pressure for an appropriate period of time.

The fitted mask can have retention members attached to it. The retention members can be any suitable members, including those as described herein. One preferred, but non-limiting type of restraining system is a PAASS. For example, before or after the moldable member, e.g., the heat-activated thermoplastic or other type of activated member, attached to the mask body is fitted, the PAASS can be attached. The PAASS can include, for example, four retention members. Each of the four retention members of the PAASS can be made of or include of an elastomeric rubber dual thimble connector and a strap of a hook and loop design. The hook and loop section is secured to one end of the elastomeric coupler by a simple double looping maneuver, and then a similar looping maneuver is used to secure the other end of the elastomeric coupler to one of four small bridges molded into the mask body. The user can then place the now custom fitted mask on their face, and secure each end of the two sets of hook and loop straps. The tension is cushioned by the elastomeric couplers, allowing for an easier fitting process. To remove the mask, the user does not have to detach the custom fitted hook and loop straps, but can instead simply stretch the attached PAASS slightly, via the elastomeric couplers, and thereby comfortably remove and replace the mask without having to reset the straps each time. As noted herein, the retention or restraining system can include a color coding system as well.

Before using the face mask, the one or more valves comprising filter elements can be secured into the mask body. Each filter can be the same, and their intended function can depend on how the filter is oriented into the mask body. The valves can have indicators to show filtered air flow direction, and the locations in the mask body that accept the valves can be shaped to fit a particular valve, for example an inhalation valve, or an exhalation valve. In this way, the filters can be of the same design and secured in the desired orientations.

Some embodiments of the face masks described herein are reusable. Typically, surgical masks are of a one-time use disposable design. The costs to hospitals of the typical disposable surgical masks is not insignificant: an average community hospital surgical operating suite incorporating eight (8) operating rooms utilizes an average of thirty (30) hospital-employed personnel, comprised of operating room nurses, surgical technicians and other circulating personnel who are in the operating room and in contact with the sterile surgical field. The typical cost to such a facility on a yearly basis for disposable surgical masks is in the range of ten thousand dollars ($10,000). Allowing for the hospital to purchase a reusable mask for each of the employed personnel would result in an anticipated savings of at least $8000 per year.

The herein described subject matter sometimes illustrates different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Hence, any two components herein combined to achieve a particular functionality can be seen as "associated with" each other such that the desired functionality is achieved, irrespective of architectures or intermedial components. Likewise, any two components so associated can also be viewed as being "operably connected", or "operably coupled", to each other to achieve the desired functionality, and any two components capable of being so associated can also be viewed as being "operably couplable", to each other to achieve the desired functionality. Specific examples of operably couplable include but are not limited to physically mateable and/or physically interacting components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

While various aspects and embodiments have been disclosed herein, other aspects and embodiments will be apparent to those skilled in the art in view of the instant disclosure. The various aspects and embodiments disclosed herein are for purposes of illustration and are not intended to be limiting, with the true scope and spirit being indicated by the following claims.

Although embodiments of the invention discussed and disclosed in the context of certain referred embodiments and examples, it will be understood by those skilled in the art that the present embodiments extend beyond the specifically disclosed embodiments to other alternative embodiments and/or uses of the embodiments and obvious modifications and equivalents thereof. In addition, while several variations of the embodiments have been shown and described in detail, other modifications, which are within the scope of these embodiments, will be readily apparent to those of skill in the art based upon this disclosure. It is also contemplated that various combination or sub-combinations of the specific features and aspects of the embodiments may be made and still fall within the scope of the inventions. It should be understood that various features and aspects of the disclosed embodiments can be combined with or substituted for one another in order to form varying modes of the disclosed embodiments. Thus, it is intended that the scope of at least some of the present technology and embodiments herein disclosed should not be limited by the particular disclosed embodiments described above.

What is claimed is:

1. A face mask, comprising:
   a generally cup shaped mask body comprising an interior surface, an opening having a peripheral edge shaped to generally follow a contour of a human face extending around at least the nasal and oral areas, a recess shaped to receive oral and nasal features of a human face, and an exterior surface opposite the interior surface, the peripheral edge having a plurality of fenestrations formed to connect both internal and external sides of the mask body;
   a first semi-pliable or metal strip on the exterior surface of the peripheral edge;
   a second semi-pliable or metal strip on the interior surface of the peripheral edge;
   a heat-activated thermoplastic member coupled to the peripheral edge, the heat-activated thermoplastic member extending over and through the plurality of fenestrations connecting both internal and external sides of the peripheral edge, thereby coupling the thermoplastic member to the mask body, and the heat-activated thermoplastic member extending around at least a portion of the peripheral edge and extending over the first semi-pliable or metal strip, over the second semi-pliable or metal strip and onto the exterior and interior surfaces of the mask body, respectively;

valves comprising at least one exhalation valve disposed on the mask body and having a first orifice that allows exhaled air to pass from an interior gas space to an exterior gas space during an exhalation, and at least one inhalation valve disposed on the mask body and having a second orifice that allows inhaled air to pass from an exterior gas space to an interior gas space during an inhalation, wherein said valves each comprise a filter element; and at least one retention member attached to said mask body.

2. The face mask of claim 1, wherein said heat-activated thermoplastic member extends for the entirety of said peripheral edge.

3. The face mask of claim 1, wherein said heat-activated thermoplastic member comprises ethylene vinyl acetate.

4. The face mask of claim 1, wherein said mask body comprises at least two exhalation valve openings disposed therein where two exhalation valves are located thereon, and a single inhalation valve opening disposed therein where said inhalation valve is located thereon, wherein the single inhalation valve is disposed at a central location on the mask body, and the two exhalation valves are disposed on an outer portion of the mask body.

5. The face mask of claim 1, wherein at least one of said at least two valves is replaceable.

6. The face mask of claim 1, wherein said filter elements are replaceable.

7. The face mask of claim 1, further comprising at least one visco-elastic member disposed on the interior of said mask body at a location alignable with a position selected from the nasal bridge of a user, and the lower chin of a user.

8. The face mask of claim 1, further comprising a generally cup shaped insert comprising an opening and a recess, the insert recess shaped to receive oral and nasal features of a human face, and said insert is adapted to be inserted into said mask body.

9. The face mask of claim 8, wherein said insert further comprises at least one exhalation valve opening disposed therein where said exhalation valve is located thereon, and at least one inhalation valve opening disposed therein where said inhalation valve is located thereon.

10. The mask of claim 1, further comprising a generally cup shaped insert positioned in the mask body comprising one or more holes or openings to permit gas or airflow through the inhalation and exhalation valves.

11. The mask of claim 1, wherein said retention member attaches to said mask body spaced away from said peripheral edge.

12. The mask of claim 1, wherein said valves are removably connected to the mask in valve housings, and wherein said valves each comprise a single replaceable unit.

13. A reusable surgical face mask, comprising:
a generally cup shaped mask body constructed of soft plastic copolymer and comprising one or more receptacles;
at least one reusable or replaceable filtered exhalation valve, wherein the at least one exhalation valve is configured to fit into a receptacle in the mask body;
at least one reusable or replaceable filtered inhalation valve wherein the at least one inhalation valve is configured to fit into a receptacle in the mask body;
a heat-activated thermoplastic member coupled to a peripheral edge of the mask, wherein the peripheral edge has a plurality of fenestrations formed to connect both internal and external sides of the mask body, wherein the heat-activated thermoplastic member extends around the entire peripheral edge of the mask and onto an exterior and an interior surface of the mask body, wherein the heat-activated thermoplastic member extends over and through the plurality of fenestrations connecting both internal and external sides of the peripheral edge, thereby coupling the thermoplastic member to the mask body, and wherein the heat-activated member comprises EVA, PO or a combination thereof; and
a passive/active adjustable strap system.

14. The mask of claim 13, wherein the mask body comprises a styrene-based thermoplastic elastomeric compound.

15. A-face mask comprising:
a generally cup shaped mask, body comprising an opening and a recess, the recess shaped to receive oral and nasal features of a human face, the opening having a peripheral edge shaped to generally follow a contour of a human face extending around at least the nasal and oral areas, the peripheral edge having a plurality of fenestrations formed to connect both internal and external sides of the mask body;
a heat-activated thermoplastic member coupled to and extending around a portion of said peripheral edge, the heat-activated thermoplastic member extending over and through the plurality of fenestrations connecting both internal and external sides of the peripheral edge, thereby coupling the thermoplastic member to the mask body;
valves comprising at least one exhalation valve disposed on the mask body and having at least one orifice that allows exhaled air to pass from an interior gas space to an exterior gas space during an exhalation, and at least one inhalation valve disposed on the mask body and having at least one orifice that allows inhaled air to pass from an exterior gas space to an interior gas space during an inhalation, wherein said at least two valves each comprise a filter element; and
at least one retention member attached to said mask body.

16. A face mask, comprising:
a generally cup shaped mask body comprising an interior surface, an opening having a peripheral edge shaped to generally follow a contour of a human face extending around at least the nasal and oral areas, a recess shaped to receive oral and nasal features of a human face, and an exterior surface opposite the interior surface;
an exhalation valve having an exhalation filter, the exhalation valve disposed on the external surface of the mask body;
an inhalation valve having an inhalation filter, the inhalation valve disposed on the external surface of the mask body;
at least one retention member attached to the external surface of the mask body;
a semi-pliable or metal strip attached to the peripheral edge of the mask body;
a plurality of fenestrations formed on the peripheral edge of the mask body, the plurality of fenestrations formed to connect both internal and external sides of the mask body; and a moldable member attached to the peripheral edge, the moldable member extending over the semi pliable or metal strip and extending over both the external and the internal surface of the peripheral edge of the mask body, and the moldable member extending over and through the plurality of the fenestrations connecting both the external and the internal surface of the peripheral edge of the mask body.

17. The face mask of claim 16, wherein the moldable member extends for the entirety of said peripheral edge.

18. The face mask of claim 16, wherein said moldable member comprises ethylene vinyl acetate.

19. The face mask of claim 16, wherein the exhalation valve is replaceable.

20. The face mask of claim 16, wherein the inhalation valve is replaceable.

21. The face mask of claim 16, wherein the exhalation filter is replaceable.

22. The face mask of claim 16, wherein the inhalation filter is replaceable.

23. The face mask of claim 16, further comprising a generally cup shaped insert comprising an opening and a recess, the insert recess shaped to receive oral and nasal features of a human face, and the insert adapted to be inserted into said mask body.

24. The face mask of claim 23, wherein the insert further comprises at least one exhalation valve opening disposed therein where the exhalation valve is located thereon, and at least one inhalation valve opening disposed therein where the inhalation valve is located thereon.

25. The face mask of claim 16, wherein the single inhalation valve is disposed at a central location on the mask body, and the exhalation valve comprises two exhalation valves disposed on an outer portion of the mask body.

* * * * *